United States Patent [19]

Dwyer et al.

[11] Patent Number: 5,986,083
[45] Date of Patent: *Nov. 16, 1999

[54] SYNTHETIC OLIGOMERS HAVING PHOSPHONATE INTERNUCLEOSIDYL LINKAGES OF UNDEFINED CHIRALITY MIXED WITH NON-PHOSPHONATE INTERNUCLEOSIDYL LINKAGES

[75] Inventors: Brian P. Dwyer; Lyle John Arnold, Jr., both of Poway; Mark Alan Reynolds, San Diego, all of Calif.

[73] Assignee: Genta, Inc., San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/340,834

[22] Filed: Nov. 17, 1994

Related U.S. Application Data

[63] Continuation-in-part of application No. 08/238,177, May 4, 1994, abandoned, and a continuation-in-part of application No. 08/233,778, Apr. 26, 1994, abandoned, and a continuation-in-part of application No. 08/154,014, Nov. 16, 1993, abandoned.

[51] Int. Cl.$^6$ ............................................ C07H 21/04
[52] U.S. Cl. ...................... 536/24.5; 536/24.3; 536/25.3; 514/44
[58] Field of Search .................... 536/24.5, 24.3, 536/25.3, 25.31; 514/44

[56] References Cited

U.S. PATENT DOCUMENTS 5,212,295  5/1993  Cook ...................................... 536/26.7

FOREIGN PATENT DOCUMENTS

92/02532  2/1992  WIPO .

*Primary Examiner*—Scott W. Houtteman
*Attorney, Agent, or Firm*—Knobbe, Martens, Olson & Bear, LLP.

[57] ABSTRACT

Oligomers having phosphonate internucleosidyl linkages mixed with non-phosphonate internucleosidyl linkages which hybridize to RNA target sequences and methods for their preparation are provided.

21 Claims, No Drawings

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:1:

CTCTCTCTCT CTCTA                            15

(2) INFORMATION FOR SEQ ID NO: 2:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:2:

CUCUCUCUCU CUCUA                            15

(2) INFORMATION FOR SEQ ID NO: 3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:3:

TCUUCCAUGC AUGUUGUCCT                    20

(2) INFORMATION FOR SEQ ID NO: 4:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (xi) SEQUENCE DESCRIPTION: SEQ ID NO:4:

GATATCTGCG GTGTCCAT                        18

SYNTHETIC OLIGOMERS HAVING PHOSPHONATE INTERNUCLEOSIDYL LINKAGES OF UNDEFINED CHIRALITY MIXED WITH NON-PHOSPHONATE INTERNUCLEOSIDYL LINKAGES

RELATED APPLICATIONS

This application is a continuation-in-part of commonly-assigned U.S. patent application Ser. No. 08/238,177, filed May 4, 1994; now abandoned, Ser. No. 08/233,778, now abandoned, filed Apr. 26, 1994; and Ser. No. 08/154,014, filed Nov. 16, 1993 now abandoned. The disclosures of which applications are incorporated by reference.

BACKGROUND AND INTRODUCTION OF THE INVENTION

The present invention is directed to synthetic Oligomers having phosphonate internucleosidyl linkages mixed with non-phosphonate internucleosidyl linkages and to methods for their synthesis.

Oligomers having naturally occurring phosphodiester internucleosidyl linkages and certain other internucleosidyl linkages do not have chiral centers at the phosphorus atom (or other atom) of the internucleosidyl linkage.

Oligomers having an alkylphosphonate or alkylphosphonothioate internucleosidyl likages have chiral centers at the phosphorus atom of the internucleosidyl linkage. These Oligomers are capable of having either Rp or Sp chirality at each phosphorus, and a particular Oligomer theoretically can have $2^n$ different diastereomeric forms where n is the number of phosphonate internucleosidyl linkages in the Oligomer. For example, an Oligomer having a total of 10 phosphonate internucleosidyl linkages theoretically has 1,024 diastereomers and an Oligomer having a total of 18 phosphonate internucleosidyl linkages theoretically has 262,144 diastereomers. Binding affinity of the oligomer to its target sequence has been reported to be affected depending on whether a phosphonate or phosphonothioate linkage has the Rp or Sp configuration.

The copending and commonly-assigned U.S. patent application Ser. No. 08/154,013, entitled "Chirally Enriched Synthetic Phosphonate Oligomers", filed Nov. 16, 1993, describes chirally enriched all-alkylphosphonate oligomers which were reported to have enhanced binding affinity for complementary RNA sequences. Synthesis of such chirally enriched oligomers may require special synthetic or purification procedures as compared with oligomers having alkylphosphonate linkages of undefined chirality ("racemic").

In a review article summarizing certain work on antisense agents, disadvantages of poorly hybridizing racemic oligodeoxynucleoside methylphosphonates in cell free extracts were said to be more or less balanced by their proposed advantages[*] in cell culture systems. It was noted that certain reports using a normal (deoxyribonucleoside) octamer with one methylphosphonate linkage found the Oligomer with an R bond to have a melting temperature higher than the Oligomer with an S bond. It was also noted that sequence dependence of methylphosphonate base pairing might be as important as chirality. (Wickstrom, "Antisense DNA Therapeutics Neutral Analogs and Their Stereochemistry" in *Gene Regulation*: Biology of Antisense RNA and DNA, 119 to 132 (Erickson and Izant, eds., Raven Press Ltd., New York (1992))

[*] Greater longevity, more efficient cellular uptake and lack of charge.

Kibler-Herzog et al., Anti-Cancer Drug Design, 8: 65–79 (1993) reported studies of melting curves for duplex and triplex formation using 19-mers having all-A or all-T sequences and alternating methylphosphonate phosphodiester, phosphodiester and predominantly methylphosphonate backbones.

Quantin and Wetmur, Biochemistry 28: 1040–1047 (1989) reported studies on the effect of ionic strength on hybridization of oligodeoxynucleotides having methylphosphonate linkages replacing certain numbers of phosphodiester linkages to unmodified oligodeoxynucleotides.

Akhtar et al., Life Sciences 49: 1793–1801 (1991) report studies on antisense DNA oligodeoxynucleotide analogs in certain cellular extracts. An oligonucleotide having alternating methylphosphonate and phosphodiester linkages was reported to have comparable stability, in terms of nuclease degradation, to the corresponding methylphosphonate and phosphorothioate oligonucleotides.

Agrawal et al, Tetrahedron Letters 28 (31): 3539–3542 (1987) reported that an oligodeoxynucleotide having two adjacent methylphosphonate replacing phosphodiester linkages at either end of an oligodeoxynucleotide increased resistance to certain nucleases.

SUMMARY OF THE INVENTION

According to one aspect, the present invention provides synthetic Oligomers which exhibit nuclease stability but yet which exhibit enhanced binding affinity to a complementary target, either RNA or DNA, in comparison with racemic all-phosphonate oligomers. Thus, the present invention provides synthetic oligomers having mixed internucleosidyl linkages, that is oligomers having phosphonate internucleosidyl linkages interspersed with single non-phosphonate, internucleosidyl linkages and methods for their preparation. Such phosphonate internucleosidyl linkages include lower alkylphosphonate internucleosidyl linkages of 1 to 3 carbon atoms and lower alkylphosphonothioate internucleosidyl linkages of 1 to 3 carbon atoms. Such non-phosphonate internucleosidyl linkages include phosphorothioate, phosphorodithioate, or phosphodiester linkages. These mixed oligomers have phosphonate internucleosidyl linkages interspersed between single non-phosphonate internucleosidyl linkages in a ratio of from 1 to about 1 to 1 to about 4 non-phosphonate linkages to phosphonate linkages. These oligomers may be used to prevent or interfere with expression or translation of a single-stranded RNA target sequence and have a nucleoside base sequence which is sufficiently complementary to the RNA target sequence to hybridize therewith. According to one preferred aspect, such Oligomers have alternating phosphonate internucleosidyl linkages which alternate with non-phosphonate internucleosidyl linkages.

In one aspect, the present invention is directed to oligomers in which the phosphonate linkages are of undefined chirality. As noted, phosphonate linkages have chiral centers at the phosphorus atom of the internucleosidyl linkage and, as such, have diasteromeric forms. Thus, such oligomers will include a mixture of diasteromers and, theoretically may have $2^m$ different diasteromeric forms for a particular oligomer, were m is the number of phosphonate linkages of undefined chirality. Such phosphonate linkages of undefined chirality also termed "racemic phosphonate linkages". The relative ratio of Rp and Sp configurations at a particular racemic phosphonate linkage may be affected by a variety of parameters including synthesis conditions, steric or position relationship of the linkage to the rest of the oligomer and other factors. We have found that by interspersing single non-phosphonate internucleosidyl linkages with racemic phosphonate linkages, oligomers which retain many of the advantages of racemic all-phosphonate oligomers, such as nuclease stability, but yet which exhibit enhanced binding in comparison with such racemic all-phosphonate oligomers are obtained. According to a preferred aspect, these oligomers have nucleosides having 2'-O-methylribose moieties as their sugars. Replacement of racemic phosphonate linkages with single non-phosphonate linkages in an oligomer of undefined chirality in a ratio of 1 to about 1 to 1 to about 4 non-phosphonate linkages to phosphonate linkages has been demonstrated to significantly enhance binding affinity of the oligomer to its complementary target and to especially increase Tm with an RNA target. Incorporation of nucleosides having 2'-O-methyl ribose sugars has been demonstrated to further enhance binding affinity.

Among other factors, the present invention is based on our unexpected finding that the mixed Oligomers described herein in which phosphonate internucleosidyl linkages are mixed with single non-phosphonate linkages display higher "net" binding affinities for their complementary RNA target sequences as compared to Oligomers of the same nucleoside base sequence having all racemic phosphonate internucleosidyl linkages. These oligomers also exhibit increased nuclease resistance as compared with oligomers having all diester, phosphorothioate or other nuclease sensitive linkages. By "net" is meant the mean of the individual binding affinities for each diastereomer in an oligomer sample. According to an especially preferred aspect, we have found that Oligomers of the present invention having nucleosides with 2'-O-methylribosyl groups as sugar moieties exhibit enhanced stability to nucleases and also exhibit increased Tm's as compared to oligomers having the same internucleosidyl linkages but with 2'-deoxyribosyl sugar moieties. In particular, we have found an increase in Tm of about 1° C. per replacement of 2'-deoxyribosyl with 2'-O-methylribosyl.

It is generally reported that DNA oligomers hybridized to either DNA or RNA targets adopt different helical geometries, termed B-form and A-form, respectively. These two different types of helices have dramatically different three dimensional shapes. Differences between the A- and B-helix forms may be summarized as follows: "An A-form duplex is generally agreed to contain sugars with a C3'-endo (N-type) pucker, in which the base pairs are inclined (tilted) approximately 19° from the helix axis and swung out from the helical axis toward the edge of the helix. As a consequence, there is greater base-base overlap in A-form structures than in B-form duplexes. In B-form duplexes of DNA, the deoxyribose sugars generally adopt a C2'-endo pucker, but with a great deal of conformational flexibility. In B-form helices, the base pairs are perpendicular to the helix axis, and are centered down the middle of the helix. There are ~11–12 base pairs per turn in an A-form duplex, and 10.4 base pairs for a B-form duplex." Hall, K. B., "NMR Spectroscopy of DNA/RNA Hybrids", *Current Opinion in Structural Biology* 3: 336–339 (1993).

Since it is known, then, that hybrids formed with DNA and RNA targets can have dramatically different geometries, one would not expect that data obtained with DNA targets would be directly applicable to RNA targets. In fact a literature report using 2'-O-methyl RNA oligomers hybridized to DNA and RNA targets supports this point (S. M. Freier et al., "Gene Regulation of Antisense RNA and DNA", pp. 95–107, edited by R. P. Erickson and J. G. Izant, Raven Press, Ltd. New York, copyright 1992). Against DNA targets, both destabilization and stabilization were observed with the 2'-O-methyl modification to the sugar portion of the nucleosides, depending on the base sequence because some DNA sequences favor the A-form more than others whereas, stabilization was always observed against RNA targets. Moreover, we have observed dramatic differences in Tm with racemic methylphosphonte oligomers hybridized to DNA and RNA targets. This suggests that evaluations of oligomers with DNA targets may give misleading results when they are intended for use as antisense inhibitors of mRNA translation.

Thus, according to one aspect, antisense Oligomers having enhanced potency in comparison to racemic all-phosphonate oligomers as antisense inhibitors of gene expression are provided which comprise Oligomers having racemic phosphonate internucleosidyl linkages which are interspersed between nuclease-sensitive internucleosidyl linkages, preferably phosphodiester linkages. For example, we have found that the Oligomers having racemic methylphosphonate linkages mixed with non-phosphonate linkages hybridize more tightly to RNA target sequences and also show enhanced potency inhibiting translation of RNA targets as compared with Oligomers having racemic all-methylphosphonate internucleosidyl linkages which did not have non-phosphonate internucleosidyl linkages.

In an alternate aspect, the present invention is directed to a synthetic Oligomer having activity in preventing or interfering with expression of a single stranded RNA target sequence which is a oligomer having racemic phosphonate internucleosidyl linkages selected from the group consisting of lower alkylphosphonate internucleosidyl linkages of 1 to 3 carbon atoms and lower alkylphosphonothioate linkages of 1 to 3 carbon atoms which are mixed with non-phosphonate internucleosidyl linkages. These mixed oligomers have phosphonate internucleosidyl linkages interspersed between single nuclease-sensitive internucleosidyl linkages and have a nucleoside base sequence which is complementary to the RNA target sequence. The mixed oligomers have a ratio of non-phosphonate to phosphonate internucleosidyl linkages of from 1 to about 1 to 1 to about 4 non-phosphonate to phosphonate linkages. Preferred phosphonate linkages include lower alkylphosphonate linkages, more preferred are methylphosphonate internucleosidyl linkages. Preferred nuclease-sensitive linkages include phosphodiester, phosphorothioate, and phosphorodithioate internucleosidyl linkages. According to an especially preferred aspect, Oligomers are provided having methylphosphonate linkages which alternate with phosphodiester linkages. These alternating oligomers have been found to exhibit enhanced binding affinity for an RNA target sequence.

According to an alternate preferred aspect, the nucleosides of these mixed oligomers have 2'-O-alkylribosyl (preferably alkyl of 1 to 3 carbon atoms), more preferably 2-O-methylribosyl, groups as sugar moieties. We have found mixed oligomers having 2'-O-methyl nucleosides and methylphosphonate linkages mixed with phosphodiester linkages to exhibit further enhancement of binding affinity to an RNA target sequence in comparison to a corresponding all-methylphosphonate oligomer of the same base sequence. These 2'-O-methyl mixed oligomers also exhibit enhanced binding affinity in comparison to corresponding mixed 2'-deoxy oligomers. We have also found that incorporation of 2'-O-methyl nucleosides in these mixed oligomers enhances stability of the oligomer to certain nucleases in comparison to oligomers having 2'-deoxynucleosides.

According to a further aspect, the present invention provides a synthetic oligomer preparation consisting of oligomers having mixed internucleosidyl linkages in which racemic phosphonate internucleosidyl linkages selected from the group consisting of lower alkylphosphonate linkages of 1 to 3 carbon atoms and lower alkylphosphonothioates of 1 to 3 carbon atoms are mixed with non-phosphonate linkages wherein the phosphonate linkages are interspersed between single non-phosphonate linkages and the oligomers are complementary to an RNA target sequence we have found that these oligomer preparations demonstrate enhanced "net" binding affinity for the RNA target sequence in comparison to racemic all-phosphonate oligomers.

In another aspect, the present invention provides methods of preparing oligomers having a predetermined base sequence of nucleosidyl units and having racemic phosphonate internucleosidyl linkages mixed with nuclease-sensitive linkages wherein the phosphonate linkages are interspersed between single non-phosphonate linkages, which methods comprise coupling to each other individual nucleoside dimers, trimers or tetramers of preselected nucleoside base sequence having phosphonate internucleosidyl linkages.

According to a further aspect, provided are synthons of the formula:

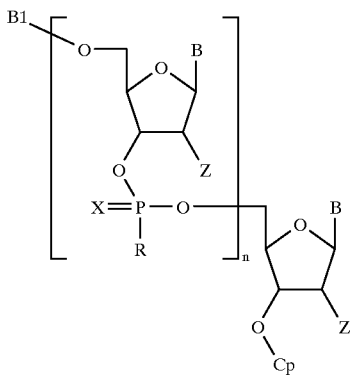

wherein X is oxygen or sulfur, R is lower alkyl of 1 to 3 carbon atoms, B1 is a blocking group removable under non-adverse conditions, Z is hydrogen, alkoxy of 1 to 10 carbon atoms, halogen or alkenyloxy of 3 to 6 carbon atoms; B is an independently selected and optionally protected purine or pyrimidine base; n is 1, 2 or 3 and Cp is a coupling group. The coupling group Cp is conveniently selected so as to give the desired nuclease-sensitive internucleosidyl linkage when coupled to another synthon.

In an especially preferred aspect, the present invention provides methods of preparing a synthetic Oligomer which exhibits enhanced binding to an RNA target sequence. In one embodiment, this method includes the steps of identifying a single stranded target sequence and synthesizing a Oligomer having a nucleoside sequence complementary to the identified RNA target sequence and having racemic phosphonate internucleosidyl linkages preferably methylphosphonate linkages, mixed with linkages, more preferably phosphodiester linkages. Such preferred Oligomers which have phosphonate linkages alternating with phosphodiester linkages exhibit enhanced binding to a RNA target sequence in comparison to an Oligomer complementary to the RNA target sequence having racemic all phosphonate internucleosidyl linkages. Alternatively, preferred oligomers include those having phosphonate linkages, preferably methylphosphonate linkages mixed with phosphorothioate linkages. According to a particularly preferred aspect, synthetic oligomers of the present invention may be synthesized by linking together nucleoside dimers, trimers or tetramers having methylphosphonate internucleosidyl linkages.

In a further aspect, the present invention provides methods for preparing an Oligomer having a predetermined base sequence of nucleoside units and which has racemic phosphonate internucleosidyl linkages mixed with non-phosphonate internucleosidyl linkages which comprises linking together individually selected synthons having racemic phosphonate internucleosidyl linkages which synthons have the formula:

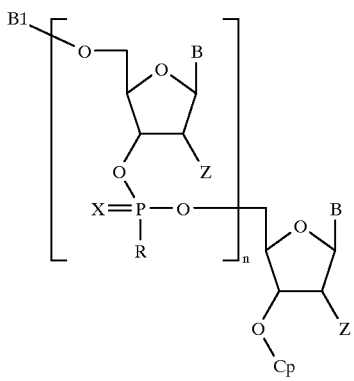

wherein X is oxygen or sulfur, R is lower alkyl of 1 to 3 carbon atoms, B is an independently selected and optionally protected purine or pyrimidine base, B1 is a blocking group, Z is hydrogen, alkoxy of 1 to 10 carbon atoms, halogen or alkenyl of 3 to 6 carbon atoms; n is 1, 2 or 3; and Cp is a coupling group selected so as to give the desired nuclease-sensitive internucleosidyl linkage when coupled to another nucleoside.

Definitions

As used herein, the following terms have the following meanings unless expressly stated to the contrary.

The term "purine" or "purine base" includes not only the naturally occurring adenine and guanine bases, but also modifications of those bases such as bases substituted at the 8-position, or guanine analogs modified at the 6-position or the analog of adenine, 2-amino purine, as well as analogs of purines having carbon replacing nitrogen at the 9-position such as the 9-deaza purine derivatives and other purine analogs.

The term "pyrimidine" or "pyrimidine base", includes not only the naturally occurring cytosine, uracil and thymine but also modifications to these bases such as 5-propymyluracil, 5-heteroaryluracils and analogs of pyrimidines such as reported heteroaromatic moieties.

The term "nucleoside" includes a nucleosidyl unit and is used interchangeably therewith, and refers to a subunit of a nucleic acid which comprises a 5-carbon sugar and a nitrogen-containing base. The term includes not only those nucleosidyl units having A, G, C, T and U as their bases, but also analogs and modified forms of the naturally-occurring bases, including the pyrimidine-analogs such as pseudoisocytosine and pseudouracil and other modified bases (such as 8-substituted purines). In RNA, the 5-carbon sugar is ribose; in DNA, it is a 2'-deoxyribose. The term nucleoside also includes other analogs of such subunits, including those which have modified sugars such as 2'-O-alkyl ribose.

The term "phosphonate" refers to the group

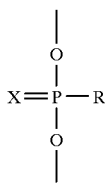

wherein X is oxygen or sulfur, R is hydrogen or an alkyl or aryl group, and thus includes various example of phosphonate and phosphonothioate internucleosidyl linkages. Suitable alkyl or aryl groups include those which do not sterically hinder the phosphonate linkage or interact with each other. The phosphonate group may exist in either an "Rp" or an "Sp" configuration. Phosphonate groups may be used as internucleosidyl linkages (or links) to connect nucleosidyl unit or a nucleosidyl unit and a non-nucleosidyl monomeric unit. The term "lower alkylphosphonate" refers to groups where X is oxygen and R is lower alkyl of 1 to 3 carbon atoms. "Methylphosphonate" refers to groups where X is oxygen and R is methyl. The term "phosphonothioate" refers to those groups where X is sulfur. The term "lower alkylphosphonothioate" refers to groups where X is sulfur and R is lower alkyl of 1 to 3 carbon atoms. The term "methylphosphonothioate" refers to a phosphonothioate group wherein R is methyl.

The term "phosphodiester" or "diester" refers to the group

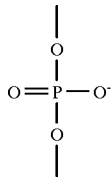

wherein phosphodiester groups may be used as internucleosidyl phosphorus group linkages (or links) to connect nucleosidyl units.

A "non-nucleoside monomeric unit" refers to a monomeric unit wherein the base, the sugar and/or the phosphorus backbone has been replaced by other chemical moieties.

A "nucleoside/non-nucleoside polymer" refers to a polymer comprised of nucleoside and non-nucleoside monomeric units.

The term "oligonucleoside" or "Oligomer" refers to a chain of nucleosides which are linked by internucleoside linkages which is generally from about 4 to about 100 nucleosides in length, but which may be greater than about 100 nucleosides in length. They are usually synthesized from nucleoside monomers, but may also be obtained by enzymatic means. Thus, the term "Oligomer" refers to a chain of oligonucleosides which have internucleosidyl linkages linking the nucleoside monomers and, thus, includes oligonucleotides, nonionic oligonucleoside alkyl- and aryl-phosphonate analogs, alkyl- and aryl-phosphonothioates, phosphorothioate or phosphorodithioate analogs of oligonucleotides, phosphoramidate analogs of oligonucleotides, neutral phosphate ester oligonucleoside analogs, such as phosphotriesters and other oligonucleoside analogs and modified oligonucleosides, and also includes nucleoside/non-nucleoside polymers. The term also includes nucleoside/non-nucleoside polymers wherein one or more of the phosphorus group linkages between monomeric units has been replaced by a non-phosphorous linkage such as a formacetal linkage, a thioformacetal linkage, a sulfamate linkage, or a carbamate linkage. It also includes nucleoside/non-nucleoside polymers wherein both the sugar and the phosphorous moiety have been replaced or modified such as morpholino base analogs, or polyamide base analogs. It also includes nucleoside/non-nucleoside polymers wherein the base, the sugar, and the phosphate backbone of the non-nucleoside are either replaced by a non-nucleoside moiety or wherein a non-nucleoside moiety is inserted into the nucleoside/non-nucleoside polymer, optionally, said non-nucleoside moiety may serve to link other small molecules which may interact with target sequences or alter uptake into target cells.

The term "neutral Oligomer" refers to Oligomers which have nonionic internucleosidyl linkages between nucleoside monomers (i.e., linkages having no positive or negative ionic charge) and include, for example, Oligomers having internucleosidyl linkages such as alkyl- or aryl-phosphonate linkages, alkyl- or aryl-phosphonothioates, neutral phosphate ester linkages such as phosphotriester linkages, especially neutral ethyltriester linkages; and non-phosphorus-containing internucleosidyl linkages, such as sulfamate, morpholino, formacetal, thioformacetal, and carbamate linkages. Optionally, a neutral Oligomer may comprise a conjugate between an oligonucleoside or nucleoside/non-nucleoside polymer and a second molecule which comprises a conjugation partner. Such conjugation partners may comprise intercalators, alkylating agents, binding substances for cell surface receptors, lipophilic agents, nucleic acid modifying groups including photo-cross-linking agents such as psoralen and groups capable of cleaving a targeted portion of a nucleic acid, and the like. Such conjugation partners may further enhance the uptake of the Oligomer, modify the interaction of the Oligomer with the target sequence, or alter the pharmacokinetic distribution of the Oligomer. The essential requirement is that the oligonucleoside or nucleoside/non-nucleoside polymer that the oligomer conjugate comprises be substantially neutral.

The term "substantially neutral" in referring to an Oligomer refers to those Oligomers in which at least about 80 percent of the internucleosidyl linkages between the nucleoside monomers are nonionic linkages.

The term "acid resistant" refers to Oligomers which are resistant, in comparison to deoxyribooligonucleotides, to acid-catalyzed depurination by hydrolysis of the N-glycosyl bond.

The term "Triplex Oligomer Pair" refers to first and second Oligomers which are optionally covalently linked at one or more sites and which are complementary to and are capable of hydrogen bonding to a segment of a single stranded target nucleic acid, such as RNA or DNA, and, thus, together with the single stranded target nucleic acid, are capable of forming a triple helix structure therewith.

The term "Third Strand Oligomer" refers to oligomers which are capable of hybridizing to a segment of a double stranded nucleic acid, such as a DNA duplex, an RNA duplex or a DNA-RNA duplex, and forming a triple helix structure therewith.

The term "complementary," when referring to a Triplex Oligomer Pair (or first and second Oligomers) or to a Third Strand Oligomer, refers to oligomers having base sequences which are capable of forming or recognizing hydrogen bonds (and base pairing or hybridizing) with the base sequence of the nucleic acid to form a triple helix structure.

The term "substantially complementary" refers to Oligomers, including Triplex Oligomer Pairs or Third Strand Oligomers which may lack a complement for each nucleoside in the target sequence, have sufficient binding affinity for the target sequence to form a stable duplex or triple helix complex, as the case may be, and thereby specifically recognize the target sequence and selectively inhibit or down-regulate its expression.

The term "triplet" or "triad" refers a hydrogen bonded complex of the bases of three nucleosides between a base (if single stranded) or bases (if double stranded) of a target sequence, a base of a Second Strand and a Third Strand (if a single stranded target sequence) or a base of a Third Strand (if a double-stranded target).

"MP" refers to a methylphosphonate internucleosidyl linkage.

"MPS" refers to a methylphosphonothioate internucleosidyl linkage.

An oligomer having "alternating MP/DE internucleosidyl linkages" refers to an Oligomer wherein methylphosphonate linkages alternate with phosphodiester linkages ("DE").

An oligomer having "alternating MP/PS internucleosidyl linkages" refers to an oligomer wherein methylphosphonate linkages alternate with phosphorothioate linkages ("PS").

An oligomer having "alternating MPS/DE internucleosidyl linkages refers to an oligomer wherein methylphosphonothioate linkages alternate with phosphodiester linkages.

An oligomer having "alternating MPS/PS internucleosidyl linkages" refers to an oligomer wherein methylphosphonothioate linkages alternate with phosphorothioate linkages.

A "MP/DE dimer synthon refers to a dinucleoside wherein the two nucleosides are linked by a mehylphosphonate internucleosidyl linkage and one of the nucleosides has a 5'- or 3'- coupling group which when coupled to a 3'-OH or a 5'-OH, of another nucleoside or an oligomer will result in a phosphodiester internucleosidyl linkage.

A "MP/PS dimer synthon" refers to a dinucleoside wherein the two nucleosides are linked by a methylphosphonate linkage and one of the nucleosides has a 5'- or 3'- coupling group which when coupled to a 3'-OH or 5'-OH of another nucleoside or an oligomer will result in a phosphorothioate internucleosidyl linkage.

A "MPS/DE dimer synthon" refers to a dinucleoside wherein the two nucleosides are linked by a methylphosphonothioate linkage and one of the nucleosides has a 5'- or 3'- coupling group which when coupled to a 3'-OH or 5'-OH of another nucleoside or an oligomer will result in a phosphodiester internucleosidyl linkage.

A "MP/PS$_2$ dimer synthon" refers to a dinucleoside wherein the two nucleosides are linked by a methylphosphonate linkage and one of the nucleosides has a 5'- or 3'- coupling group which when coupled to a 3'-OH or 5'-OH of another nucleoside or an oligomer will result in a phosphorothioate internucleosidyl linkage.

A "2'-O-methyl MP/2'-O-methyl DE dimer synthon" refers to a dinucleoside wherein two 2'-O-methyl nucleosides are linked by a methylphosphonate linkage and one of the nucleosides has a 5'- or 3'-coupling group which when coupled to a 3'-OH or 5'-OH of another nucleoside or an oligomer will result in a phosphodiester internucleosidyl linkage.

DETAILED DESCRIPTION OF THE INVENTION

The phosphonate internucleosidyl linkages used in oligomers of the present invention contain an lower alkyl group replacing one of the two non-bonding (or non-bridging) oxygens on the phosphorus of a phosphodiester internucleosidyl linkage, the other non-bonding oxygen remains or is alternatively replaced by sulfur. The replacement of oxygen by lower alkyl creates a chiral environment around the phosphorus which can be designated as either Rp or Sp, depending on which of the non-bonding oxygens has been replaced with lower alkyl. The Rp and Sp configurations can be depicted as follows:

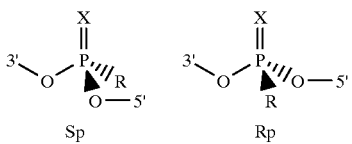

wherein X is oxygen or sulfur and R is lower alkyl. Since the mixed oligomers having phosphonate linkages mixed with non-phosphonate linkages are capable of having either Rp or Sp chirality at each phosphonate linkage, a particular Oligomer theoretically can have $2^n$ different diastereomeric forms where n is the number of phosphonate internucleosidyl linkages in the Oligomer. For example, an Oligomer having 10 phosphonate internucleosidyl linkages theoretically has 1,024 diastereomers and an Oligomer having 18 phosphonate internucleosidyl linkages theoretically has 262,144 diastereomers.

In one aspect, the present invention is directed to methods of synthesizing Oligomers having racemic phosphonate internucleosidyl linkages mixed with non-phosphonate internucleosidyl linkages.

According to one preferred synthetic method, nucleoside dimers having a racemic phosphonate linkage connecting the two nucleosidyl units of the dimer are prepared. The resulting dimers are then derivatized so that they may be coupled together using an automated DNA synthesizer (see, e.g., Examples 1 to 4). The dimers may have coupling groups which result in any one of a variety of internucleosidyl linkages between dimers. From a stock of 16 dimers, oligomers of any nucleoside base sequence may be synthesized by linking together the appropriate dimers. Dimers are added to the growing Oligomer chain until an Oligomer having the desired number of nucleosides is obtained. The resulting Oligomer has a phosphonate at every other internucleosidyl linkage (i.e., those linkages originally derived from the coupled dimeric units). The remaining internucleosidyl linkages comprise non-phosphonate internucleosidyl linkages, such as phosphodiester, phosphorothioate, phosphorodithioate, morpholino, phosphoramidite, phosphorofluoridate, boranophosphate, formacetal, silyl or other non-phosphonate internucleosidyl linkages.

Alternatively, larger blocks of nucleosides such as trimers and tetramers may be coupled. Trimers having two phosphonate internucleosidyl linkages may be conveniently prepared by coupling the appropriate dimer synthon to nucleoside monomer. The resulting trimer has phosphonate linkages at both internucleosidyl linkages. The trimers are then derivatized to give trimer synthons so that they may be coupled together using an automated DNA synthesizer. The trimer synthons have coupling groups which allow them to be coupled together to give a phosphonate oligomer. From a stock of 64 trimers, oligomers of any base sequence may be synthesized by linking together the appropriate trimers. Trimers may be sequentially added to the growing oligomer chain or alternatively coupled with nucleoside monomers, dimers and/or tetramers until an oligomer having the desired number of nucleosides is obtained. The resulting oligomer has a phosphonate linkage at those internucleosidyl linkages derived from the internucleosidyl linkages of the coupled dimers, trimers or tetramers. Thus, use of these trimers will result in an oligomer having phosphonate linkages at about two out of every three internucleosidyl linkages. By following analogous techniques, tetramers having three phosphonate internucleosidyl linkages may be prepared and coupled to each other to give oligomers. Alternatively, dimers, trimers and other short oligomers having phosphonate internucleosidyl linkages may be coupled together in appropriate sequence to give an oligomer of a particular desired base and internucleosidyl linkage sequence and length.

The phosphonate dimers and trimers described in the Examples and Detailed Description herein can be coupled together by a variety of different methods leading to the following, non-exclusive, types of internucleosidyl linkages: phosphodiester, phosphotriester phosphorothioate, phosphorodithioate, phosphoramidate, phosphorofluoridates, boranophosphates, formacetal, and silyl.

Internucleosidyl phosphodiester linkages can be obtained by converting the 3'-OH of a dimer or trimer to either a phosphotriester synthon (Reese, C. B. (1978) Tetrahedron 34, 3142–3179), phosphoramidite synthon (Beaucage, S. L. and Lyer, R. P. (1992) Tetrahedron 48, 2223–2311), H-phosphonate synthon (Froehler, B. C. in Agrawal, S., ed. Protocols for oligonucleotides and Analogs, Synthesis and Properties, Methods in Molecular Biology Vol. 20, Humana Press, Totowa, N.J., 1993, pp. 63–80), or phosphorornonochloridite reagent (Hogrefe, R. I. (1987) dissertation, Northwestern University, Evanston, Ill.).

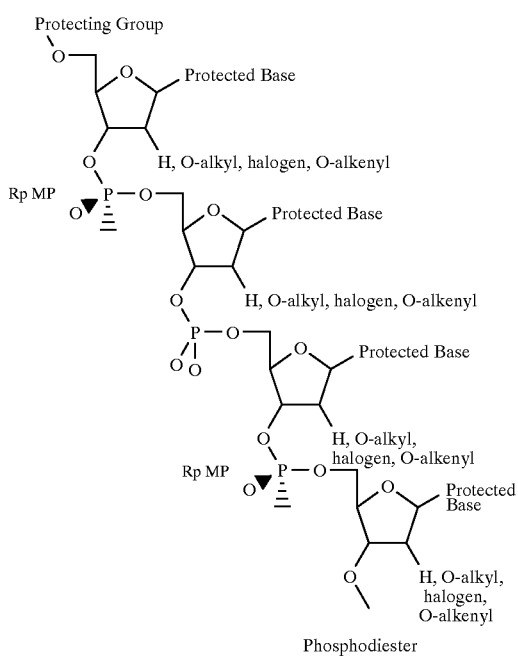

Phosphodiester

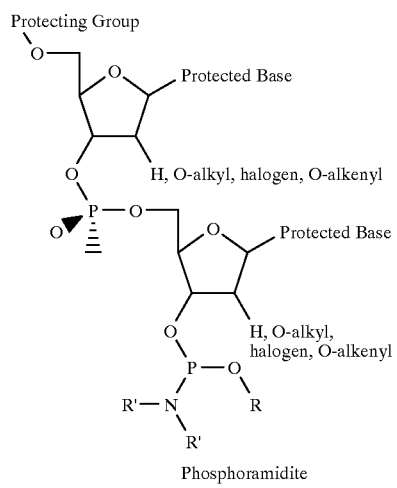

Phosphoramidite

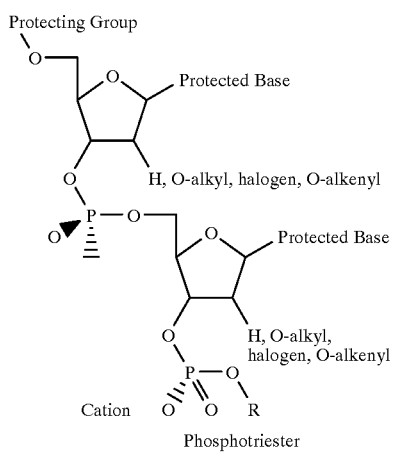

Phosphotriester

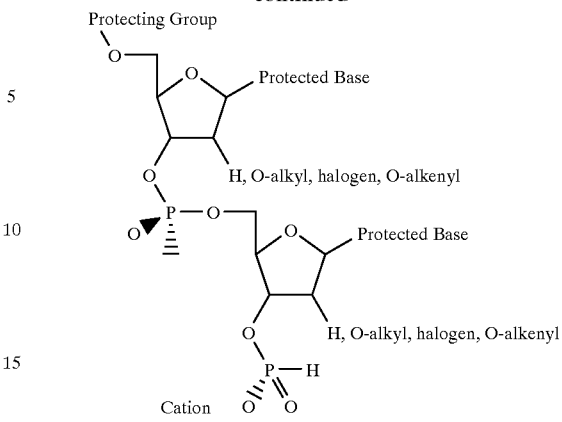

H-Phosphonate

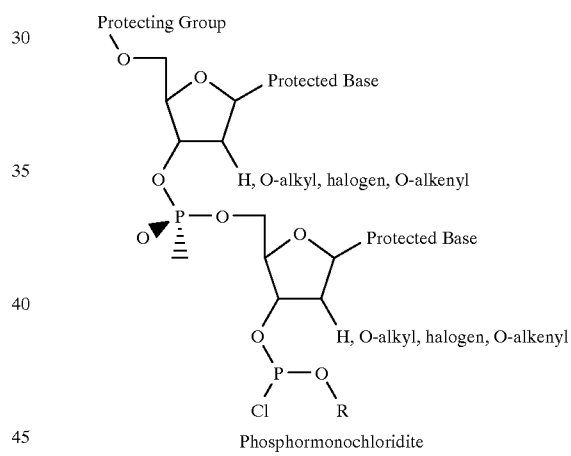

Phosphormonochloridite

Internucleosidyl phosphorothioate linkages can be obtained by converting the 3' OH of a dimer or trimer to either a phosphotriester synthon (Stec, W. J., et al. (1991) Nucl. Acids Res. 19, 5883–5888)), phosphoramidite synthon (Lyer, R. P., et al. (1990) JACS 112, 1254–1255), H-phosphonate synthon (Seela, F. and Kretschmer U. (1991) J. Org. Chem. 56, 3861–3869), or phosphoromonochloridite reagent (Hogrefe, R. I. (1987) Dissertation, Northwestern University, Evanston, Ill.).

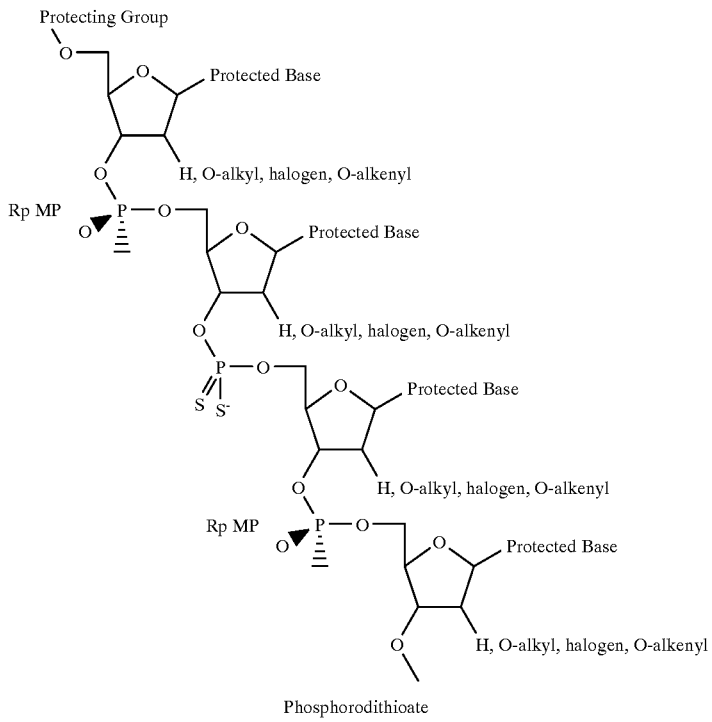

Phosphorodithioate

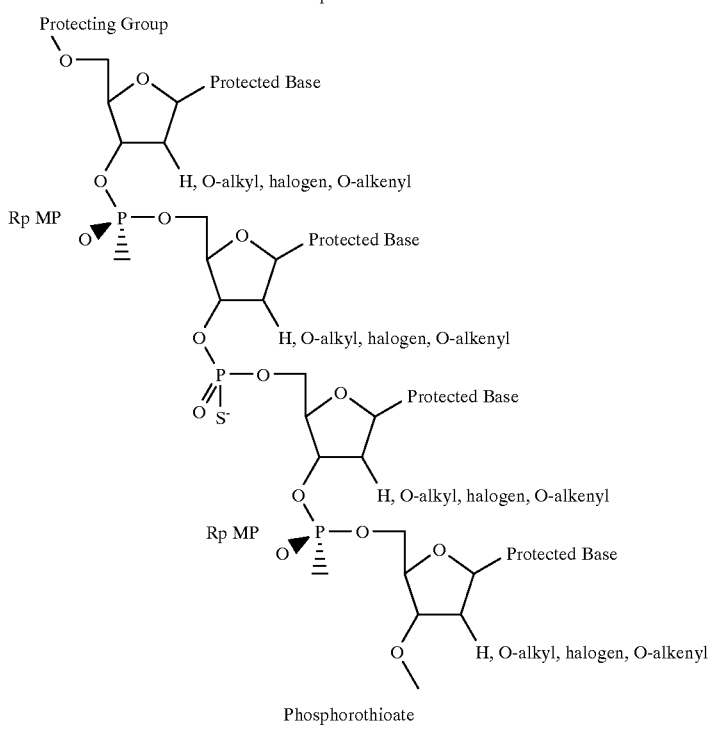

Phosphorothioate

Internucleosidyl phosphorodithioate linkages can be prepared as by the Example herein and by U.S. Pat. No. 5,218,088 to Gorenstein et al. Internucleosidyl phosphotriester linkages can be obtained by converting the 3'-OH of a dimer or trimer to either a phosphotriester synthon (Reese, C. B. (1978) Tetrahedron 34, 3143–3179), phosphoramidite synthon (Beaucage, S. L. and Lyer, R. P. (1992) Tetrahedron 48, 2223–2311), H-phosphonate synthon (Froehler, B. C. in Agrawal, S., ed. Protocols for Oligonucleotides and Analogs, Synthesis and Properties, Methods in Molecular Biology Vol. 20, Humana Press, Totowa, N.J., 1993, pp. 63–80), phosphoromonochloridite reagent (Hogrefe, R. I. (1987) Dissertation, Northwestern University, Evanston, Ill.), or post synthetically (see U.S. Pat. No. 5,023,243 to Tullis.

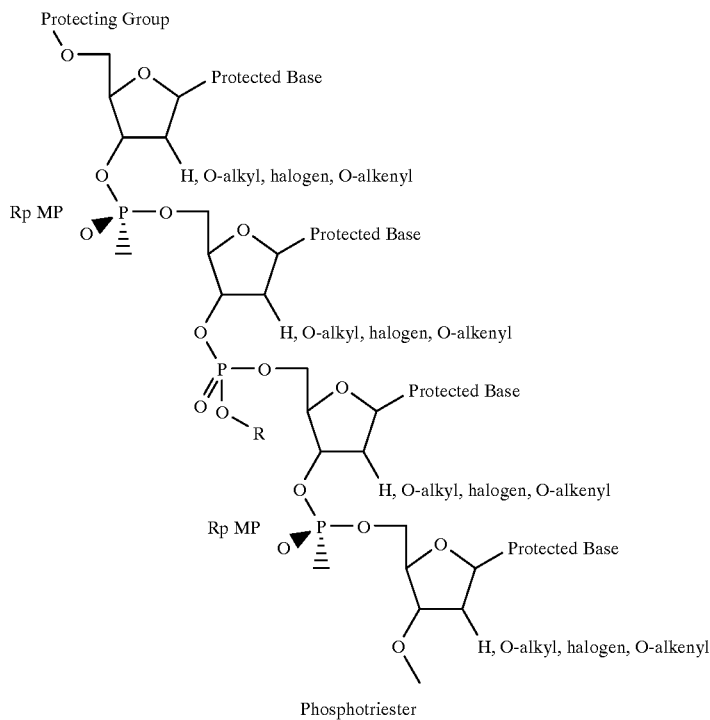

Phosphotriester

Internucleosidyl phosphoramidate, phosphorofluoridate, boranophosphate, formacetal, and silyl linkages can be obtained by converting the 3' OH of a dimer or trimer to the appropriate synthons. (See Agrawal, S., ed. Protocols for Oligonucleotides and Analogs, Synthesis and Properties, Methods in Molecular Biology Vol. 20, Humana Press, Totowa, N.J., 1993, for synthetic protocols to obtain synthons for each of the above.)

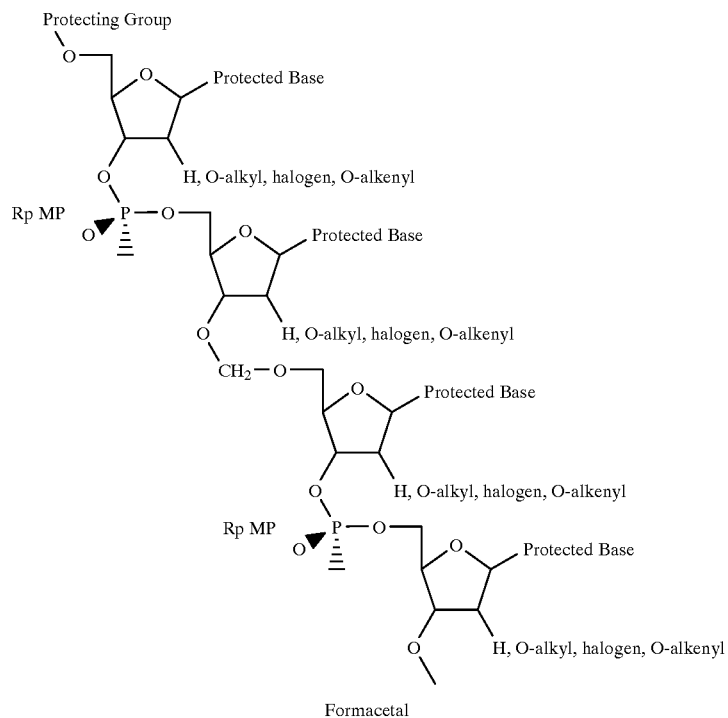

Formacetal

-continued
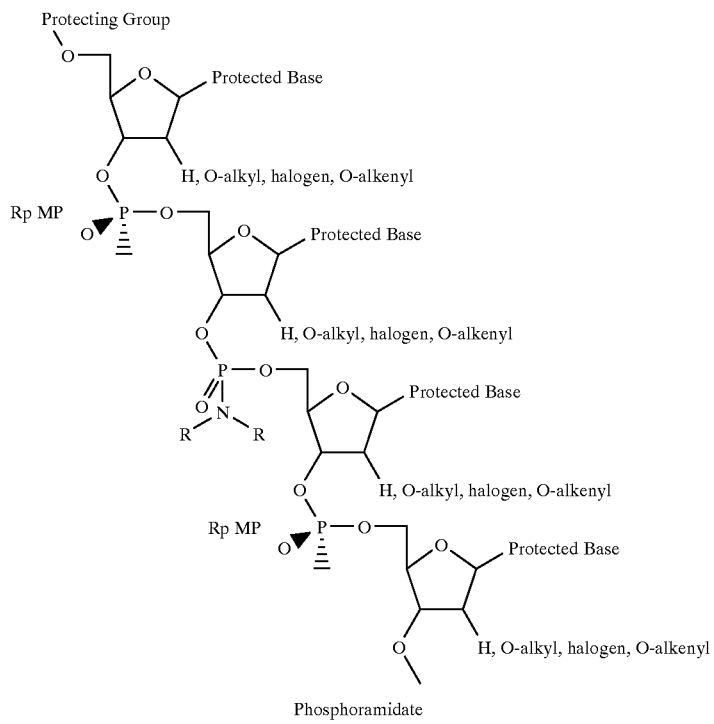
Phosphoramidate
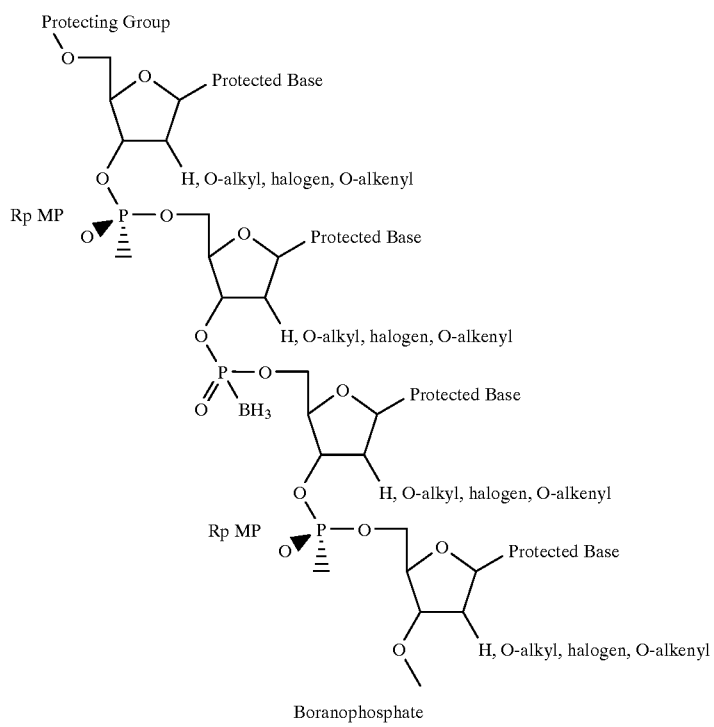
Boranophosphate

-continued

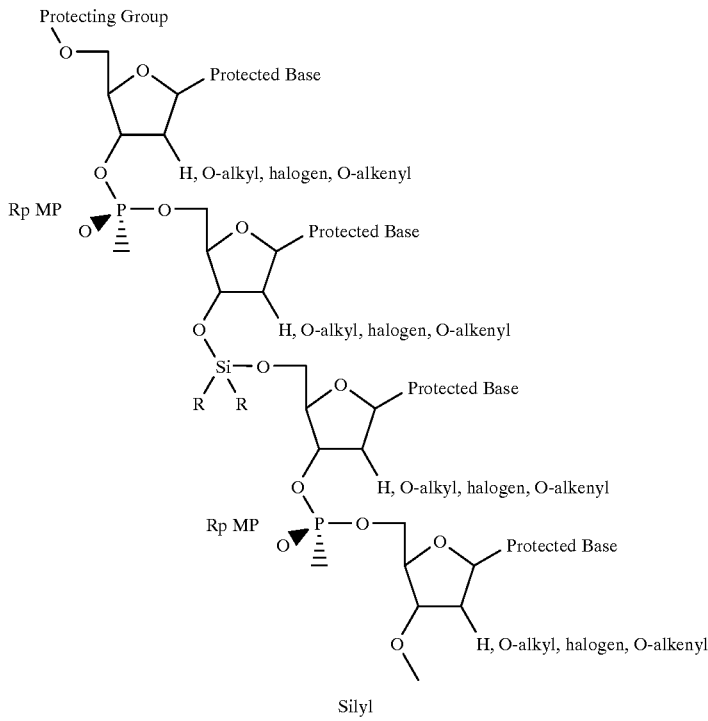

Silyl

Utility and Administration

The Oligomers provided herein may form a high affinity complex with a target sequence such as a nucleic acid with a high degree of selectivity. In addition, derivatized oligomers may be used to bind with and then irreversibly modify a target site in a nucleic acid by cross-linking (psoralens) or cleaving one or both strands (EDTA). By careful selection of a target site for cleavage, one of the strands may be used as a molecular scissors to specifically cleave a selected nucleic acid sequence. Alternatively, the Oligomers of the present invention may include an RNase H activating sequence.

According to one aspect of the present invention, these antisense Oligomers have a sequence which is complementary to a portion of the RNA transcribed from a selected target gene. Although the exact molecular mechanism of inhibition has not been conclusively determined, it has been suggested to result from formation of duplexes between the antisense oligomer and the RNA transcribed from the target gene. The duplexes so formed may inhibit translation, processing or transport of an mRNA sequence.

According to an alternate aspect of the present invention, interference with or prevention of expression or translation of a selected RNA target sequence may be accomplished by triple helix formation using Oligomers of the present invention as a Triplex Oligomer Pair having sequences selected such that the oligomers are complementary to and form a triple helix complex with the RNA target sequence and thereby interfere with or prevent expression of the targeted nucleic acid sequence. Such triple strand formation can occur in one of several ways. Basically, two separate or connected Oligomers may form a triple strand with the single stranded RNA. Further descriptions of the use of oligomers (including Triplex Oligomer Pairs) to prevent or interfere with the expression of a target sequence of double or single stranded nucleic acid by formation of triple helix complexes is described in the copending U.S. patent applications Ser. Nos. 07/388,027, 07/751,813, now U.S. Pat. No. 5,565,541, 07/772,081 and 07/987,746 now abandoned, the disclosures of which are incorporated herein by reference.

As a general matter, the oligomers employed will have a sequence that is complementary to the sequence of the target nucleic acid. However, absolute complementarity may not be required; in general, any oligomer having sufficient complementarity to form a stable duplex (or triple helix complex as the case may be) with the target nucleic acid is considered to be suitable. Since stable duplex formation depends on the sequence and length of the hybridizing Oligomer and the degree of complementarity between the antisense Oligomer and the target sequence, the system can tolerate less fidelity (complementarity) when longer Oligomers are used. This is also true with Oligomers which form triple helix complexes. However, Oligomers of about 8 to about 40 nucleosidyl units in length which have sufficient complementarity to form a duplex or triple helix structure having a melting temperature of greater than about 40° C. under physiological conditions are particularly suitable for use according to the methods of the present invention.

With respect to single stranded target sequences, we have found that two strands of a methylphosphonate Oligomer having methylphosphonate linkages (Second and Third Strands) and one strand of a complementary synthetic RNA Oligomer (First Strand) may form a triple helix complex. According to those experiments, the two methylphosphonate strands bind in a parallel orientation. Experiments described triple helix formation with methylphosphonate Oligomers of random sequence of A and G nucleosides which would not make triple helix complexes according to any of the "classical" triplet motifs.

These triple helix complexes formed by binding a target single stranded RNA and two methylphosphonate Oligomers show high affinity (Tm>50° C.). Formation of these triple helix complexes has been shown to dramatically inhibit translation at sub-micromolar concentrations.

The triple helix complexes can be formed using Oligomers containing naturally occurring bases (i.e., A, C, G, T or U). Alternatively, if desired for increased stability, certain stabilizing bases such as 2-amino A (for A) or 5-methyl C may be used in place of the corresponding naturally occurring base. These bases may increase stability of the triple helix complex by having increased hydrogen bonding interactions and stacking interactions with other bases. Increased stability may result in increased affinity constants which increase potency.

The Oligomers provided herein may be derivatized to incorporate a nucleic acid reacting or modifying group which can be caused to react with a nucleic acid segment or a target sequence thereof to irreversibly modify, degrade or destroy the nucleic acid and thus irreversibly inhibit its functions.

These Oligomers may be used to inactivate or inhibit or alter expression of a particular gene or target sequence of the same in a living cell, allowing selective inactivation or inhibition or alteration of expression. The target sequence may be DNA or RNA, such as a pre-mRNA or an mRNA. mRNA target sequences include an initiation codon region, a coding region, a polyadenylation region, an mRNA cap site or a splice junction. These Oligomers could also be used to permanently inactivate, turn off or destroy genes which produced defective or undesired products or if activated caused undesirable effects.

Since the oligomers provided herein may form duplexes or triple helix complexes or other forms of stable association with transcribed regions of nucleic acids, these complexes are useful in "antisense" or triple strand therapy. "Antisense" therapy as used herein is a generic term which includes the use of specific binding Oligomers to inactivate undesirable DNA or RNA sequences in vitro or in vivo.

Many diseases and other conditions are characterized by the presence of undesired DNA or RNA, which may be in certain instances single stranded and in other instances in double stranded. These diseases and conditions can be treated using the principles of antisense therapy as is generally understood in the art. Antisense therapy includes targeting a specific DNA or RNA target sequence through complementarity or through any other specific binding means, in the case of the present invention by formation of duplexes or triple helix complexes.

The Oligomers for use in the instant invention may be administered singly, or combinations of Oligomers may be administered for adjacent or distant targets or for combined effects of antisense mechanisms with the foregoing general mechanisms.

In therapeutic applications, the Oligomers can be formulated for a variety of modes of administration, including oral, topical or localized administration. It may be beneficial to have pharmaceutical formulations containing acid resistant Oligomers that may come in contact with acid conditions during their manufacture or when such formulations may themselves be made acidic, to some extent, in order to more compatible with the conditions prevailing at the site of application, e.g., the acid mantle of the skin. Techniques and formulations generally may be found in *Remington's Pharmaceutical Sciences*, Mack Publishing Co., Easton, Pa., latest edition. The Oligomer active ingredient is generally combined with a carrier such as a diluent or excipient which may include fillers, extenders, binding, wetting agents, disintegrants, surface-active agents, erodible polymers or lubricants, depending on the nature of the mode of administration and dosage forms. Typical dosage forms include tablets, powders, liquid preparations including suspensions, emulsions and solutions, granules, and capsules.

Certain of the Oligomers of the present invention may be particularly suited for oral administration which may require exposure of the drug to acidic conditions in the stomach for up to about 4 hours under conventional drug delivery conditions and for up to about 12 hours when delivered in a sustained release from. For treatment of certain conditions it may be advantageous to formulate these Oligomers in a sustained release form. U.S. Pat. No. 4,839,177 to Colombo et al., the disclosure of which is incorporated herein by reference, describes certain preferred controlled-rate release systems. For oral administration, these oligomers have 2'-O alkyl nucleosidyl units; these Oligomers are formulated into conventional as well as delayed release oral administration forms such as capsules, tablets, and liquids.

The Oligomers having 2'-O-alkyl nucleosidyl units may be particularly suited for formulation in preparations for topical administration, since the skin has an acid mantle, formulations including these acid resistant Oligomers may prove advantageous. This also can be advantageous in light of the finding that neutral Oligomers will cross skin and mucous membranes as described in U.S. patent application Ser. No. 07/707,879 which is incorporated by reference. Also it may be desirable to provide formulations which include acidic media when using acid-resistant neutral Oligomers.

For topical administration, the Oligomers for use in the invention are formulated into ointments, salves, eye drops, gels, or creams, as is generally known in the art.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucusal administration. In addition, detergents may be used to facilitate permeation. Transmucosal administration may be through use of nasal sprays, for example, as well as formulations suitable for administration by inhalation, or suppositories.

To assist in understanding the present invention, the following examples are included which describe the results of a series of experiments. The following examples relating to this invention should not, of course, be construed in specifically limiting the invention and such variations of the invention, now known or later developed, which would within the purview of one skilled in the art are considered to fall within the scope of the present invention as hereinafter claimed.

EXAMPLES

Example 1

Preparation of a MP/DE Dimer Synthon

A. Preparation of a (CT) Dimer Having a Methylphosphonate Internucleosidyl Linkage Using Solution Phase Chemistry Into a 2 L roto-evaporator flask was placed 10.0 g (28 mM) of 3'-tert-butyldimethylsilyl thymidine and 26.1 g (35 mM) of 5'-dimethoxytrityl-$N^4$-isobutyryl-3'-methyl-N,N-diisopropylaminophosphoramidite-2'-deoxycytidine. The solids were dissolved in 500 ml of acetonitrile and evaporated to dryness under vacuum. This process was repeated with another 500 ml of acetonitrile and then the flask was released under argon and stoppered with a rubber septa.

This dry solid foam was then dissolved in 500 ml of acetonitrile ("ACN"), and with manual stirring, treated all at once with 404 ml tetrazole (180 mM, 0.45 M tetrazole in THF). Manual stirring is continued for 30 seconds and then the flask is allowed to stand for another 2.5 minutes, after which time the reaction mix is treated all at once with 275 ml of an oxidizer solution ($I_2/H_2O$/lutidine/THF; 25 g/2.5 ml/100 ml/900 ml). The solution was stirred manually and allowed to stand at room temperature for 15 minutes. The resulting dark amber solution was then treated with bisulfite (2 g/25 ml/$H_2O$), which upon addition, turned the solution light amber as it reacted with the excess iodide. The reaction mix was then concentrated to a thick oil and taken up in ethyl acetate ("EtOAc") (500 ml) and washed with saturated sodium bicarbonate (2×250 ml) and $H_2O$ (2×250 ml). The organic phase was dried over $MgSO_4$, filtered and concentrated to a light colored solid foam, which upon further drying yielded 35 grams of crude dimer.

The Rp diastereomer was separated on normal phase silica using a methanol step gradient in 75/25 EtOAc/$CH_2Cl_2$. A 7.5 cm by 60 cm column, was loaded with 700 g of silica (first slurried in 2.5 L of neat 75/25 EtOAc/$CH_2Cl_2$). The crude dimer was then dissolved in 75 ml of 75/25 EtOAc/$CH_2Cl_2$ and loaded onto the column. The column was started with 1% methanol and increased to 2% and finally 3% where the Rp dimer began to elute. The Rp dimer eluted cleanly over several bed volumes while maintaining 3% methanol in the eluent. The Sp dimer was eluted later with 30% methanol. The Rp dimer yield was 11.0 grams, while the Sp yield was 17.8 grams. HPLC analysis (ACNMETH) was performed on the Rp dimer and one peak was observed at 14.5 minutes. The tlc (75/25 EtOAc/$CH_2Cl_2$, 5% methanol) of this product, revealed a single spot product with an Rf of 0.55 which, upon treatment with 10% sulfuric acid in ethanol and heat, was both trityl and sugar positive.

The Rp/SP mixture is dissolved in ACN and treated all at once at room temperature with 22 ml TBAF (0.022 M, 1 M in THF). The reaction mixture is allowed to stand overnight at ambient temperature. Completion of the reaction is monitored by TLC (75/25, EtOAc/$CH_2Cl_2$ with 10% methanol), when no starting material is detected but a small amount of 5'-DMT-dT may observed, which runs considerably faster on normal phase silica than the 3'-OH of the dimer. The reaction mixture is concentrated on a rotary evaporator to a thick oil which is then dissolved in $CH_2Cl_2$ (200 ml) and washed with saturated sodium bicarbonate (2×100 ml) and $H_2O$ (2×100 ml). The organic phase is dried over $MgSO_4$, filtered, and concentrated to a light yellow solid foam, which was purified on 100 grams of silica (75/25, EtOAc/$CH_2Cl_2$ with 5% methanol).

B. Preparation of a (CT) MP(Rp/Sp)/DE Dimer Synthon

Into a 100 ml round bottom flask is placed 0.5 g (0.55 mMol) CT-3'-OH dimer (product of Example 1A) which is rendered anhydrous by 3×20 ml co-evaporations with pyridine. The flask is released from the vacuum system under argon gas and stoppered with a rubber septa. The compound is redissolved in 10 ml acetonitrile and 200 μl (1.4 mMol, 2.5 eq) TEA were added. To the resulting mixture at room temperature and with manual stirring, is added in one portion 200 μl (0.90 mmol, 1.6 eq.) 2'-cyanoethyl-N,N-diisoprophylchlorophosphoramidite. The reaction mixture is allowed to sit at room temperature before being analyzed by reverse phase HPLC. The HPLC (Beckman System Gold, C18 bondapak, ACN method Solution A was 50/50 ACN/0.1 M TEAA in water, pH 7 and Solution B was ACN. A gradient of 0 to 100% Solution B is run at a rate of 1 ml/minute over 25 minutes) showed complete conversion of starting material and a crude purity of greater than 90 percent. The reaction mixture was concentrated under vacuum to a light yell solid foam. The foam is purified immediately by chromatography on 20 g of normal flash grade silica equilibrated with 5/1/5 ethyl acetate/acetonitrile/methylene chloride with 2% TEA to give the above-identified product.

Example 2

Preparation of 2'-O-Methyl MP(Rp)/2'-O-Methyl DE Dimer Synthons

A. Preparation of 2'-O-Methyl C Monomer

A 5.0 g (8 mmol) portion of 2'-O methyl cytidine is rendered anhydrous with pyridine co-evaporations (3×25 ml) and is then dissolved in 50 ml acetonitrile. The solution is treated with 1.65 ml triethylamine ("TEA") (12 mmol, 1.5 eq.) and cooled in an ice bath. The solution is then treated with dropwise addition of 1.65 ml chloromethyl-N,N-diisopropylamino phosphine ("Cl-MAP") over two minutes. The ice bath is removed and the reaction mixture stirred for two hours. The reaction mixture (reaction is determined to be complete by HPLC) is concentrated to dryness. The residue is dissolved in 20 ml ethyl acetate/heptane (1:1) with 4% TEA, then loaded onto 40 g silica gel equilibrated with the same solvent system. All UV absorbing eluent from the column is collected and pooled, then is concentrated to give 5.5 g of the above-identified product (yield about 90%).

B. Preparation of Silyl-Protected 2'-O-Methyl Uridine

Into a 250 ml round bottom flask is placed 5.0 g (9.0 mmol) 5'-DMT, 2'O-methyl uridine which is rendered anhydrous with dimethylformamide (DMF) co-evaporations (3×25 ml). The resulting dry foam is taken up in 50 ml DMF, is then treated all at once with 2.4 g (35 mmol, 3.9 eq.) imidazole, is then followed by dropwise addition of 3.0 ml (12 mmol, 1.3 eq.) t-butyldiphenylsilyl chloride. The reaction mixture is stirred at room temperature overnight.

The progress of the reaction is checked by HPLC (ACN method) and thin layer chromotography ("TLC") using 5% methanol in methylene chloride, and is determined to be complete when no starting material is evident. The reaction mixture is then poured into ice water and taken up in methylene chloride, then washed several times with aqueous sodium bicarbonate and water. The organic phase is dried over magnesium sulfate, filtered and then concentrated to give 7.2 g of a solid foam which gives a single spot on TLC. The solid foam is then dissolved in 70 ml methylene chloride and treated (with rapid magnetic stirring) all at once with 70 ml. benzene sulfonic acid, 2% by weight in 2:1 methylene chloride/methanol. After stirring for 15 minutes at room temperature, the reaction mixture is quenched with 10 ml TEA. The resulting detrilylated compound is stripped down to a thick amber oil which was then loaded onto 150 g. silica gel equilibrated in heat methylene chloride. The product is eluted from the column using 2% methanol (in methylene chloride). After drying, the above identified product is obtained.

C. Preparation of 2'-O-Methyl (CU) Dimer

The silyl-protected 2'-O methyl uridine monomer (product of Example 2B) (3.0 g, 6 mmol) is taken up in 30 ml anhydrous ACN. The 2'-O methyl cytidine amidite monomer (product of Example 2A) (5.5 g, 7 mmol, 1.2 eq.) separately, is taken up in 55 ml ACN. Both solutions are allowed to stand over 3 Å molecular sieves overnight at room temperature.

The two solutions are carefully decanted into a single flask and treated with 94 ml tetrazole (0.45 M in ACN, 42 mmol, 7 eq). The resulting mixture is stirred for 4 minutes and then oxidized by addition of 1.5 ml (1.2 eq.) cumene hydroperoxide. The reaction mixture is concentrated to dryness, then taken up in methylene chloride and is washed with aqueous sodium bicarbonate and water. The organic phase is dried over magnesium sulfate, filtered and concentrated to give 7.5 g. of a solid foam.

The Rp/Sp racemic mixture is isolated by column chromatography using two silica columns (100:1, silica to crude product, equilibrated in 3:1 ethylacetate/methyl chloride with an increasing methanol gradient from 1 to 5%).

D. Deprotection of 2'-O-Methyl Rp/Sp(CU) Dimer A 1.07 g (0.90 mmol) portion of the 2'-O methyl CU dimer (product of Example 2C) is dissolved in 10 ml THF and treated all at once with 1.5 ml (1 m in THF, 1.5 eq.) tetrabutylammonium fluoride ("TBAF"). The reaction mixture is stirred at room temperature or 30 minutes. The reaction mixture is concentrated and the concentrate is purified on silica gel, eluting with 3:1 ethyl acetate/methylene chloride with 5% methanol. The clean fractions concentrated to give the above-identified pure 5'-OH dimer.

E. Preparation of a 2'-O-Methyl (CU) MP(Rp/Sp)/DE Dimer Synthon

A portion of 2'-O-methyl CU 3'-OH dimer (product of Example 2D) is rendered anhydrous by 2 co-evaporations in ACN. The resulting dry solid foam is dissolved in 2.5 ml ACN and then 73 $\mu$l (2.5 eq.) triethylamine ("TEA") and 94 $\mu$l (2.0 eq.) 2'-cyanoethyl-N,N-diisopropyl chlorophosphoramidite (ACNE) is added. The reaction mixture is stirred at room temperature for 2 hours and completion of the reaction determined by HPLC. The reaction mixture is dissolved in eluent (3/1/1 ethylacetate/acetonitrile/methylene chloride with 4% TEA) and loaded onto 2 g silica gel equilibrated with 3/1/1 ethylacetate/acetonitrile/methylene chloride with 4% TEA. The column is run using 3/1/1 ethylacetate/acetonitrile/methylene chloride with 1% TEA. The clean fractions, 3 to 25, are concentrated, redissolved in acetonitrile and concentrated again to a solid foam. The foam is dried overnight under full vacuum to give 200 mg of the above-identified product.

Example 3
Preparation of 2'-O Methyl MPS/ 2'-O Methyl-DE Dimer Synthons

These dimer synthons are prepared by following the procedures described in Example 2, except that in Paragraph c, an equivalent amount of 3H-1,2-benzodithiole-3-one, 1,1-dioxide (Beaucage reagent) is substituted for cumene hydroperoxide.

Example 4
Preparation of MPS/DE Dimer Synthons

These dimer synthons are prepared by following the procedures of Example 1, except in Paragraph A, an equivalent amount 3-H-1,2-benzodithiole-3-one, 1,1-dioxide (Beaucage reagent) is substituted for the oxidizer solution ($I_2/H_2O$/lutidine/THF)

Example 5
Preparation of MP/PS$_2$ Dimer Synthons

The MP/(Rp)/PS$_2$ (phosphorodithioate) dimer synthons are prepared as follows.

Dinucleosides having a free 3'-OH are prepared according to the methods described in Examples 1A.

The dinucleoside is converted to the corresponding thiophosphoramidite using procedures such as those of Plotto et al. (Plotto et al, Tetrahedron 47: 2449–61 (1991)) or Gorenstein et al., U.S. Pat. No. 5,218,088.

The dinucleoside is co-evaporated three times with anhydrous pyridine, followed by three co-evaporations with toluene.

A portion of dinucleoside (10 mmoles) is dissolved in 200 ml anhydrous dichloromethane, then three equivalents of anhydrous diisopropylethylamine followed by 1.5 equivalents of chloro-N,N-diisopropylaminothiomethoxyphosphine are added at 0° C. with stirring. The reaction is monitored by TLC until determined to be complete.

The product is worked up and purified using the procedures of Example 1B for isolation of the MP/DE phosphoramidite.

Example 6
Preparation of MPS/PS$_2$ Dimer Synthons

The MPS/PS$_2$ dimer synthons are prepared as follows. The dinucleoside with a free 3'-OH is prepared according to the methods of Example 4. Using the dinucleoside, the dimer synthon is prepared by the methods of Example 5.

Example 7
Preparation of MPS/2'-O Methyl DE Dimer Synthons

The MPS/2'-O-methyl DE dimer synthons are prepared using procedures analogous to those of Examples 1 and 3 but using the appropriate protected 2'-deoxynucleoside and protected 2'-O-methyl nucleosides.

Example 8
Preparation of an Oligomer Having Alternating MP/DE Internucleosidyl Linkages An oligomer having the sequence 5'-(CT)-(CT)-(CT)-(CT)-(CT)-(CT)-(CT)-A-3' [SEQ. ID. NO. 1] was prepared using a CT MP/DE dimer synthon prepared according to Example 1. The grouped dinucleosides indicate the methylphosphonate linkages.

Manual couplings are used to synthesize the oligomer to conserve reagent, although the process can be done on an automated DNA synthesizer. The sequence was synthesized from the 3'-terminus starting with methacrylate support bound deoxyadenosine.

The protected dinucleoside methylphosphonamidite (22 mg each per required coupling) freshly co-evaporated with pyridine and toluene to ensure dryness are placed into dried 1 ml glass autosampler vials and are dissolved in anhydrous acetonitrile to a concentration of 0.1 M (200 $\mu$l per coupling). The vessels are purged with argon and tightly sealed with screw caps with teflon septa.

A 1 $\mu$mole scale DNA synthesis column (Milligen) is filled with 1 $\mu$mole of methacrylate support bound deoxyadenosine. The column is attached to a ring stand in a vertical orientation. A male-male leur fitting is attached to the bottom along with an 18 gauge needle to control the effluent. The column is washed with 10 ml acetonitrile using a syringe. The support bound nucleoside is detritylated by passing 3 ml of 2% dichloroacetic acid in dichloromethane through the column over 1.5 minutes. The orange, dimethoxytrityl cation bearing solution is reserved. The column is washed twice with 10 ml each of anhydrous acetonitrile.

The first coupling is accomplished as follows: 10 ml more anhydrous acetonitrile is passed through the column. Then, 200 $\mu$l of the CT methylphosphonamidite is drawn into a 1 ml syringe. Next, 200 $\mu$l of 0.45 M tetrazole in anhydrous acetonitrile is likewise drawn into the syringe containing the methylphosphonamidite. The reagents are rapidly mixed in the syringe, then are slowly passed through the column dropwise over three minutes, being sure to lightly draw the plunger up and down to ensure adequate mixing with the support. After 3 minutes, 1 ml of the oxidizing reagent (0.1 M I$_2$ in 73% tetrahydrofuran, 25% 2,6-lutidine and 2% water) is passed through the column over one minute. The column is washed with 20 ml acetonitrile and then is treated with 600 $\mu$l of a solution containing 20% (v/v) acetic anhydride, 30% (v/v) acetonitrile, 50% (v/v) pyridine and 0.312% (w/v) dimethylaminopyridine. The column is then washed with 20 ml acetonitrile.

The above-described synthetic cycle is repeated until the synthesis is completed.

The oligomer is then cleaved from the support and deprotected. The support bound oligomer is removed from the synthesis cartridge and is placed in a glass 1 dram vial with a screw top. The support is treated for 30 minutes at room temperature with 1 ml of a solution of acetonitrile/ethanol/NH$_4$OH (9/9/1). Then, 1 ml of ethylenediamine is added to the reaction vessel and the reaction is allowed to sit for 6 hours at ambient temperature in order to go to completion. The supernatant containing the oligomer is then removed from the support and the support is rinsed twice with 2 ml of 1/1 acetonitrile/water; the washings were combined with the supernatant. The combined solution is diluted to 30 ml total volume with water and neutralized with approximately 4 ml of 6 N HCL. The neutralized solution is desalted using a Waters C-18 Sep-Pak cartridge which is pre-equilibrated with 10 ml acetonitrile, 10 ml of 50% acetonitrile/100 mM triethylammonium bicarbonate, and 10 ml of 25 mM triethylammonium bicarbonate, sequentially. After the reaction solution is passed through the column, it is washed with 30 ml of water. The product is then eluted with 5 ml of 1/1 acetonitrile/water.

The oligomer is purified on HPLC using a Beckman Ultrasphere-reverse phase 4.5×250 mm column with an increasing gradient of acetonitrile in 0.5 M triethylammonium acetate (0% to 40% over 40 minutes). The isolated yield is 41 OD$_{260}$ units (35%). The compound is characterized by electron spray mass spectrometry.

Alternatively, the above-identified oligomer can be synthesized on an automated DNA synthesizer. In which case the appropriate dimer synthons (as used above in the manual synthesis) are dissolved in acetonitrile to a concentration of 0.1 M as described above. The amidite solutions are placed in conical vessels on a Millipore Expedite DNA Synthesizer. All other reagents (oxidizer, deblock, capping reagents and activator) are prepared as described above for the manual synthesis, and applied to the appropriate positions on the instrument as instructed in the manual. Table I gives programming parameters for one synthesis cycle. The deprotection and purification of the oligomer is carried as described above for the manually synthesized oligomer.

TABLE I

| Function | | Mode | Amount/ Arg1 | Time(sec)/ Arg2 | Description |
|---|---|---|---|---|---|
| $Deblocking | | | | | |
| 144 /* Advance Frac | */ | NA | 1 | 0 | "Event out ON" |
| 0 /* Default | */ | WAIT | 0 | 1.5 | "Wait" |
| 141 /* Photometer S | */ | NA | 1 | 1 | "START data collection" |
| 16 /* Dblk | */ | PULSE | 10 | 0 | "Dblk to column" |
| 16 /* Dblk | */ | PULSE | 100 | 49 | "Deblock" |
| 38 /* Wsh A to C1 | */ | PULSE | 80 | 0 | "Flush system with Wsh A" |
| 39 /* Gas A to C1 | */ | PULSE | 20 | 0 | "Gas A to C1 waste" |
| 141 /* Photometer S | */ | NA | 0 | 1 | "STOP data collection" |
| 144 /* Advance Frac | */ | NA | 2 | 0 | "Event out OFF" |
| $Coupling | | | | | |
| 1 /* Wsh | */ | PULSE | 5 | 0 | "Flush system with Wsh" |
| 2 /* Act | */ | PULSE | 5 | 0 | "Flush system with Act" |
| 25 /* 8 + Act | */ | PULSE | 6 | 0 | "Monomer + Act to column" |
| 25 /* 8 + Act | */ | PULSE | 1 | 8 | "Couple monomer" |
| 2 /* Act | */ | PULSE | 4 | 31.9 | "Couple monomer" |
| 1 /* Wsh | */ | PULSE | 7 | 55.9 | "Couple monomer" |
| 1 /* Wsh | */ | PULSE | 8 | 0 | "Flush system with Wsh" |
| $Capping | | | | | |
| 12 /* Wsh A | */ | PULSE | 20 | 0 | "Flush system with Wsh A" |
| 13 /* Caps | */ | PULSE | 8 | 0 | "Caps to column" |
| 12 /* Wsh A | */ | PULSE | 6 | 15 | "Cap" |
| 12 /* Wsh A | */ | PULSE | 14 | 0 | "Flush system with Wsh A" |
| $Oxidizing | | | | | |
| 17 /* Aux | */ | PULSE | 15 | 0 | "Aux Ox for b-CE" |
| 12 /* Wsh A | */ | PULSE | 15 | 0 | "Flush system with Wsh A" |
| $Capping | | | | | |
| 13 /* Caps | */ | PULSE | 7 | 0 | "Caps to column" |
| 12 /* Wsh A | */ | PULSE | 50 | 0 | "Wsh A" |
| 12 /* Wsh A | */ | PULSE | 100 | 0 | "End of cycle wash" |

Example 9

Preparation of an Oligomer Having Alternating 2'-O-Methyl MP(Rp/Sp)/2'-O-Methyl DE Internucleosidyl Linkages An oligomer having the sequence 5'(CU)-(CU)-(CU)-(CU)-(CU)-(CU)-(CU)-A-3' [SEQ. ID. NO. 2] was prepared using 2'-O-methyl MP(Rp)/2'-O-methyl DE dimer synthons prepared according to Example 2 hereinabove.

The appropriate dimer synthons are dissolved in acetonitrile to a concentration of 0.1 M. All other reagents used are as described in Example 8.

A 1 μmole scale DNA synthesis column (Millipore) was filled with 1 μmole of methacrylate support bound deoxyadenosine. The dimer synthons are coupled sequentially from the 3'-terminus as described in Example 8 except that the coupling time was extended to two minutes. The dimethoxytrityl is removed from the oligomer at the end of the synthesis.

The deprotection is carried out as described in Example 8. The oligomer is purified on HPLC with a Beckman Ultrasphere-RP using an increasing gradient of acetonitrile in 0.5 M triethylammonium acetate (10% to 30% over 30 minutes). The compound is characterized by electron spray mass spectrometry.

This oligomer can also be synthesized on an automated DNA synthesizer as follows. The appropriate dimer synthons (as used above in the manual synthesis are dissolved in acetonitrile as described in Example 8. The amidite solutions are placed in conical vessels on the Millipore Expedite DNA synthesizer. All other reagents (oxidizer, deblock, capping reagents and activator) are prepared as described in Example 8, and are applied to the appropriate positions on the instrument as instructed by the manual. The same coupling program as described in Example 8 is used except that the coupling time is extended to 2 minutes.

The deprotection is carried out as described in Example 8. The oligomer can be purified on HPLC using as described above for the manual synthesis.

Example 10
Preparation of an Oligomer Having Alternating MP/PS Internucleosidyl Linkages An oligomer having alternating MP/PS internucleosidyl linkages is prepared using the dimer synthons used in Example 8. All the parameters of the synthesis, deprotection and purification are as described in Example 8, except that the oxidizing reagent is replaced by a 0.1 M solution of 3H-1,2-benzodithiole-3-one, 1,1-dioxide or a 0.1 M solution of sulfur in 1/1 carbon disulfide/diisopropylethylamine.

Example 11
Preparation of an Oligomer Having Alternating MPS/DE Internucleosidyl Linkages An oligomer having alternating MPS/DE internucleosidyl linkages is prepared using the dimer synthons of Example 4. All other parameters of synthesis, deprotection and purification are as described in Example 8.

Example 12
Preparation of an Oligomer Having Alternating MPS/PS Internucleosidyl Linkages An oligomer having alternating MPS/PS internucleosidyl linkages is prepared using the dimer synthons of Example 4. All of the parameters of synthesis, deprotection and purification are as described in Example 8, except that the oxidizing reagent is replaced by a 0.1 M solution of 3H-1,2-benzodithiole-3-one, 1,1-dioxide or a 0.1 M solution of sulfur in 1/1 carbon disulfide/diisopropylethylamine.

Example 13
Preparation of an Oligomer Having Alternating MP/PS$_2$ Internucleosidyl Linkages An oligomer having alternating MP/PS$_2$ internucleosidyl linkages is prepared using the dimer synthons of Example 5. All of the parameters of synthesis, deprotection and purification are as described in Example 12.

Example 14
Preparation of an Oligomer Having Alternating MPS/PS$_2$ Internucleosidyl Linkages An oligomer having alternating MPS/PS$_2$ internucleosidyl linkages is prepared using the dimer synthons of Example 6. All of the parameters of the synthesis, deprotection and purification are as described in Example 12.

Example 15
Preparation of an Oligomer Having Alternating MP/2'-O-Methyl DE Internucleosidyl Linkages An oligomer having alternating MP/2'-O-Methyl DE internucleosidyl linkages is prepared using the dimer synthons of Example 7. All other parameters of synthesis, deprotection and purification are as described in Example 9.

Example 16
Preparation of 2'-F Dimer Synthons

Dimer synthons useful in the preparation of the oligomers of the present invention may be prepared using 2'-fluoronucleosides. Methods for preparation of 2'-fluoronucleosides have been reported and are known to those skilled in the art. (See, e.g.: Codington, JOC Vol. 29 (1964) (2'-F U); Mangel, Angew. Chem. 96: 557–558 (1978) and Doen, JOC 32: 1462–1471 (1967) (2'-F C); Ikehara, Chem. Pharm. Bull. 29: 1034–1038 (1981) (2'-F G); Ikehara, J. Carbohydrates, Nucleosides, Nucleotides 7: 131–140 (1980) (2'-F A], and also Krug, A, Nucleosides & Nucleotides 8: 1473–1483 (1989).

The preparation of dimer synthons using 2'-fluoronucleosides may be accomplishing using the procedures analogous to those described for the 2'-O-methyl dimer synthons (See, e.g., Examples 2, 3, and 5). The resulting dimer synthons may be used to prepare oligomers using methods analogous to the methods used for the 2'-O methyl dimer synthons such as Examples 9 and 15.

Example 17
Preparation of 2'-O-Allyl Dimer and Trimer Synthons and Their Use in Oligomer Synthesis The dimer and trimer synthons described in Examples 1, 4 and 14 can be prepared using 2'-O-allyl nucleosides. The preparation of 2'-O-allyl nucleosides has been reported and they are commercially available, as has been reported there use in the preparation of oligomers. (See, e.g., Iribarren, et al. (1990) Proc. Natl. Acad. Sci. (USA) 87: 7747–51; and Lesnik et al. (1983), Biochemistry 32: 7832–8). The nucleosides are used to prepare dimer and trimer synthons using procedures described hereinabove. The synthons are used to prepare oligomers using methods such as those described in Examples 5, 6, 7, 9, 12, 13 or 15.

Example 18
Preparation of a MP(Rp)/MP Dimer Synthon
A. Preparation of a (CT) Dimer Having a Chirally Pure Methylphosphonate Internucleosidyl Linkage Using Solution Phase Chemistry Into a 2 L roto-evaporator flask is placed 10.0 g (28 mM) of 3'-tert-butyldimethylsilyl thymidine and 26.1 g (35 mM) of 5'-dimethoxytrityl-N$^4$-isobutyryl-3'-methyl-N,N-diisopropylaminophosphoramidite-2'-deoxycytidine. The solids are dissolved in 500 ml of acetonitrile and evaporated to dryness under vacuum. This process is repeated with another 500 ml of acetonitrile and then the flask is released under argon and stoppered with a rubber septa.

This dry solid foam is then dissolved in 500 ml of acetonitrile ("ACN"), and with manual stirring, treated all at once with 404 ml tetrazole (180 mM, 0.45 M tetrazole in THF). Manual stirring is continued for 30 seconds and then the flask is allowed to stand for another 2.5 minutes, after which time the reaction mix is treated all at once with 275 ml of an oxidizer solution (I$_2$/H$_2$O/lutidine/THF; 25 g/2.5 ml/100 ml/900 ml). The solution is stirred manually and allowed to stand at room temperature for 15 minutes. The resulting dark amber solution is then treated with bisulfite (2 g/25 ml/H$_2$O), which upon addition, turned the solution light amber as it reacted with the excess iodide. The reaction mix is then concentrated to a thick oil and taken up in ethyl acetate ("EtOAc") (500 ml) and washed with saturated sodium bicarbonate (2×250 ml) and $H_2O$ (2×250 ml). The organic phase is dried over $MgSO_4$, filtered and concentrated to a light colored solid foam, which upon further drying yielded 35 grams of crude dimer.

The crude dimer is run on HPLC (reverse phase, Waters C18 bondapak) with a program (ACNMETH) starting with 50% acetonitrile and 0.1 M triethylammonium acetate (TEAA, pH ~7.0) which increased to 100% acetonitrile over 20 minutes with a linear gradient. Two major peaks are resolved, one at 4.5 minutes, which is residual lutidine and the other at 14.5 minutes which is the mixture of Rp and Sp diastereomers. The ratio of Rp and Sp is determined quantitatively by taking a 5 mg aliquot of the crude product and dissolving it in 1.5 ml of acetonitrile along with 0.5 ml of tetrabutylammonium fluoride (TBAF, 1 M solution in THF).

The dimer, 11.0 g (0.011 M) is dissolved in 110 ml of ACN and treated all at once at room temperature with 22 ml of TBAF (0.022 M, 1 M in THF). The reaction mix was allowed to stand overnight at ambient temperature. The next morning the reaction is determined to be complete by TLC (75/25 EtOAc/$CH_2Cl_2$, 10% methanol); no starting material is detected but a small amount of 5'-DMT-dT was observed, which runs considerably faster on normal phase silica than the 3'-OH of the dimer. The reaction mixture is concentrated on a rotary evaporator to a thick oil which is then dissolved in $CH_2Cl_2$ (200 ml) and is washed with saturated sodium bicarbonate (2×100 ml) and $H_2O$ (2×100 ml). The organic phase was dried over $MgSO_4$, filtered, and concentrated; the concentrate is purified on silica (75/25, EtOAc/$CH_2Cl_2$ with 5% methanol).

B. Preparation of a (Rp/Sp) Dimer Synthon

The CT-3'-OH dimer, prepared as described and hereinabove, is rendered anhydrous with two co-evaporations with pyridine. The resulting solid foam is released from the rotary evaporator with argon and stoppered with a rubber septa. The solid foam is dissolved in 100 ml of 9/1, ACN/$CH_2Cl_2$, then treated with 1.7 ml triethylamine (TEA, 12 mM). With magnetic stirring, the reaction mix is treated dropwise at room temperature with 1.5 ml chloromethyl-N,N-diisopropylamino phosphine (Cl-MAP, 8 mM). The reaction is monitored on HPLC (ACNMETH).

The reaction mixture is concentrated on a rotary evaporator using a partial vacuum; the flask which contained the resulting light amber sludge is released under argon and capped. The crude product is immediately passed through a flash column containing 60 grams of silica (first equilibrated in 1/1/1 ACN/EtOAc/$CH_2Cl_2$ with 3% TEA). The product is eluted quickly with this eluent and all U.V. positive fractions are pooled and concentrated. The resulting solid concentrate is co-evaporated with ACN to remove any residual TEA, then dried overnight under full vacuum to give the final product.

Example 19
Preparation of MP/MP/DE Trimer Synthons

The above-identified trimer synthon is prepared using the dimer synthons of Example 18. The dimer synthon is coupled to a 5'-OH,3'-silylated nucleoside according to the methods of Example 18A for the coupling of the 3'-nucleoside to the monomer phosphoramidite.

The selected 5'-OH,3'-silylated nucleoside (1 equivalent) and dimer methylphosphonamide (1.25 equivalents) are weighed into a round bottom flask and dried by co-evaporation with acetonitrile. The resulting foam is dissolved in acetonitrile and treated with a solution of 0.45 M tetrazole in acetonitrile (4.5 equivalents). After 3 minutes, the reaction mixture is oxidized and the reaction product is worked up as described in Example 18A. The trimer is converted to a trimer synthon by reaction with chloro-β-cyanoethoxy-N,N-diisopropylaminophosphoramidite using methods as described in Example 1B. The trimer synthon is worked up and purified using methods as described in Example 1B.

Example 20
Preparation of an Oligomer Having MP/MP/DE Internucleosidyl Linkages

The above-identified oligomer is prepared using the trimer synthons of Example 19 and by following the methods described in Example 8, substituting the trimer synthons for dimer synthons. All other parameters of synthesis, deprotection and purification are as described in Example 8.

Example 21
Preparation of a 2'-O-Me-GG (5'O-DMT, 3'O-βCE, $N^2$IBU) MP Dimer Via a 5'-Methylphosphonamidite Monomer Into a 500 ml RBF was placed 30.5 g (0.05 M) of 2'-OMe-G(3'O-tBDPS,5'-OH, $N^2$IBU) which was rendered anhydrous with 1×100 ml pyridine and 2×100 ml acetonitrile (ACN). The resulting dry foam was released from the roto-evaporator with argon and treated with 300 ml anhydrous ACN, 10.5 ml triethylamine (0.075 M, 1.5 eq.). The flask was stoppered with a rubber septa and treated (dropwise) with 10.9 ml chloromethyl-N,N-diisopropylaminophosphine (0.06 M, 1.2 eq.). The reaction was allowed to stir overnight at room temperature.

The next morning, the reaction was found to contain no starting material, as determined by HPLC (Beckman Gold, RP, Waters C18 bondapak; λ254 nm, 20 minute program 50/50 ACN/0.1 M TEAA to 100% ACN.). The reaction mixture was concentrated then purified on 225 g silica in 3:1 ethyl acetate/heptane containing 2% TEA. Product was pooled and concentrated to obtain 25 g (67%) of solid foam that was 86% pure by HPLC. This product was taken up in ACN to give a 10% solution of the desired amidite, which was stored over molecular sieves.

Into a 500 ml flamed dried RBF with argon balloon overhead, was transferred via an addition funnel with glass wool, 100 ml (10 g, 0.013M, 1.25 eq.) of stock solution of 2'O-Me-G(5'-amidite, 3'-tBDPS, $N^2$IBU) along with 71.1 ml (7.1 g, 0.011 M 1.0 eq.) of stock solution of 2'O-Me-G (5'DMT, 3'OH, $N^2$IBU). The reaction mixture was then treated all at once with 30.9 ml (25% by weight sol. in ACN, 5.0 eq.) of ethylthio-tetrazole (ETT) and stirred at room temperature for 5 minutes, after which time cumene hydroperoxide (2.1 ml, tech., 80%) was added all at once. The reaction was quenched 5 minutes later with 20 ml saturated sodium bisulfite. The reaction mixture was analyzed by HPLC and determined to be 86% dimer with a ratio of 1.2/1.0 (Sp/Rp). The reaction mixture was then placed on a roto-evaporator and the ACN was removed. The resulting concentrate was then taken up in 150 ml dichloromethane (DCM), and washed; 2×75 ml sat. $NaHCO_3$ and 1×75 ml water. The aqueous washes were combined and then extracted 1×75 ml with DCM and combined with the original organic phase and dried over $NaSO_4$, filtered and concentrated to a light amber solid foam.

The solid foam, 12.6 g (0.0094 M, 1.0 eq.) of 2'-O-Me-GG(5'DMT, 3'tBDPS, $N^2$-iBu) MP(Rp/Sp) product was taken up in 120 ml of THF and treated all at once with 14.2 ml TBAF (1M in THF, 0.014 M, 1.5 eq.) and allowed to stand at room temperature overnight. The next morning desilylation was determined to be complete by HPLC with a purity of 84% (44% Sp and 40% Rp).

Example 22
Preparation of 2'-O-Me-CU(5'-DMT, 3'-OH, N$^4$IBU) MP(Rp) Dimer Via a 3'-Methylphosphonamidite Monomer 50 g (0.082 M, 1.0 eq.) of the 2'-O-Me-DMT protected cytidine was rendered anhydrous with 3×100 ml pyridine and 1×100 ml ACN co-evaporations. The flask was released with argon and to it was added a stir bar, 500 ml ACN, 22.7 ml TEA (0.163 M, 2 eq.) and a septa with an argon balloon overhead. The solution was treated dropwise with 19.2 ml (0.11 M, 1.3 eq.) of Cl-MAP via a 20 ml plastic syringe and stirred overnight at room temperature. The reaction was checked the next morning on HPLC and starting material was gone. The reaction mixture was concentrated and purified on 300 g silica gel with 50/50, EtOAc/Heptane, with 2% TEA. Four liters of the eluent were passed through the column and all U.V. positive material was pooled and concentrated to a solid foam (52 g, 95% purity (HPLC), 84% recovery). The product was taken up in ACN to give a 10% solution by weight of the desired 3'-methylphosphonamidite and to this solution was added molecular sieves.

After sitting over molecular sieves for one night, 100 ml (10 g, 0.013 M, 1.25 eq.) of this stock solution was added to a flame dried 500 ml round bottom flask along with 51 ml of a stock solution of U, 5'-OH (5.1 g, 0.01 M, 1.0 eq.). The ETT (67 ml, 10% solution in ACN over molecular sieves, 6.7 g, 0.052 M, 5.0 eq.) was added all at once via an addition funnel and the reaction was stirred for 5 minutes at room temperature. The phosphite intermediate was then oxidized with 36 mls of camphor sulfonyl oxaziridine (CSO) solution (10% in ACN over molecular sieves) for 5 minutes. The reaction mixture was checked by HPLC and found to contain 79% dimer with a ratio of 1.2/1.0 (Sp/Rp). The reaction mixture was concentrated to a solid foam, taken up in 150 ml DCM and worked up as described above in example 19. The resulting solid foam was 89% dimer by HPLC and was desilylated (see below) without further purification.

The solid foam, 2'-O-Me-CU(5'-ODMT, 3'-OtBDPS, N$^4$IBU), MP(Sp/Rp), dimer, was taken up in 100 ml THF then treated all at once with 12.3 ml tetrabutyl ammonium fluoride (1 M in THF, 0.012 M, 1.5 eq.). The reaction was checked 1 hour later by HPLC and determined to be complete by the disappearance of starting material. The reaction mixture was concentrated and purified on silica gel (10:1) with 3:1 EtOAc:DCM with 10% methanol.

Example 23
Preparation of 2'-Me-G(5'-OH, 3'-OtBDPS, N$^2$IBU) Via the DMT Protected 3'-OH 25 g of DMT protected 2'-O-Me-guanosine was rendered anhydrous with 3×100 ml DMF co-evaporations. The solid foam was released from the roto-evaporator via argon and dissolved in 250 ml anhydrous DMF. The solution was then treated with 15.3 g of t-butyldiphenylsilyl chloride (0.056 M, 1.5 eq.) and 10.1 g imidazole (0.15 M, 4.0 eq.), then stirred manually until the solution was homogeneous and allowed to let stand overnight at room temperature. The reaction was checked by HPLC the next morning and found to contain no starting material. The reaction mixture was then poured into 300 ml ice water while manually stirring. The solids were collected in a buchner funnel and rinsed with cold water and then dissolved in 250 ml DCM and washed with 3×200 ml sat. NaHCO$_3$ and 1×100 ml water. The combined aqueous phases were extracted with 2×100 ml DCM. The organic phases were combined and dried over NaSO$_4$, filtered and concentrated to a solid foam, obtaining 35 g of newly silylated product (slightly more than theoretical).

The solid foam, 2'-O-Me-G(5'-ODMT, 3'-OtBDPS, N$^2$IBU) was dissolved in 150 ml DCM and with magnetic stirring was treated all at once with 260 ml benzene sulfonic acid (0.1 M solution in 75/25 DCM/MeOH, 0.026 M, 0.67 eq.). The reaction was allowed to proceed for 10 minutes after which time a TLC in 5% MeOH in DCM revealed that complete desilylation had occurred. The reaction was immediately quenched with 20 ml TEA, at which time the solution changed from a deep clear amber color to a light clear yellow color. The solution was concentrated to a thick oil and then loaded onto 250 g silica gel equilibrated in 0.5% MeOH in DCM. The free trityl was removed with the same eluent and the product was then removed with 6% MeOH in DCM. The fractions containing product were pooled and concentrated to obtain 21.8 (98.5% pure by HPLC, 91% yield overall) of the titled compound.

Example 24
Preparation of 2'-O-Me UC(5'-ODMT, N$^4$IBU)-3'CE Phosphoramidite Via UC, 3'-OH 980 mg of 2'-O-Me UC (5'DMT, 3'OH, N$^4$IBU) MP dimer is rendered anhydrous with 3×10 ml ACN co-evaporations. The resulting dry foam is then taken up in 10 ml anhydrous ACN and to it is added 325 μl TEA (2.32 mmol, 2.25 eq.), followed by dropwise addition (via a 1 ml glass syringe) of 460 μl 2'-cyanoethyl-N,N-diisopropyl chlorophosphoramidite (2.06 mmol, 2.0 eq.). The reaction is allowed to stir overnight, after which time completion of the reaction is checked by TLC and HPLC. The reaction mixture is concentrated and loaded onto a 1.5×20 cm column containing 30 g silica equilibrated in 3:1:1, EtOAc:DCM:ACN with 1% TEA. The product is eluted in the same mixture and the fractions with pure product are pooled and concentrated to yield the amidite.

Example 25
Synthesis and Purification of 2'-O-Methyl Oligomer With Alternate Methylphosphonate-Diester Backbone (a) Reagents and Materials
Synthesis reagents
MAP Monomers: 5'-Dimethoxytrityl-N$^4$-isobutyryl-2'-O-methylcytidine-3'-(N,N-diisopropylmethylphosphonamidite ($C_{me}$-MAP), 5'-Dimethoxytrityl-N$^2$-isobutyryl-2'-O-methylguanosine-3'-(N,N-diisopropyl-methylphosphonamidite ($G_{me}$-MAP), 5'-Dimethoxytrityl-2'-O-methyluridine-3'-(N,N-diisopropyl-methylphosphonamidite ($U_{me}$-MAP), and N$^6$-Benzoyl-5'-Dimethoxytrityl-2'-O-methyladenosine-3'-(N,N-diisopropyl-methylphosphonamidite ($A_{me}$-MAP).

2-Cyanoethyl Monomers: 5'-Dimethoxytrityl-N$^4$-isobutyryl-2'-O-methylcytidine-3'-[2-cyanoethyl-N,N-diisopropyl-phosphoramidite] ($C_{me}$-DE), 5'-Dimethoxytrityl-N$^2$-isobutyryl-2'-O-methylguanosine-3'[2-cyanoethyl-N,N-diisopropyl-phosphoramidite] ($G_{me}$-DE),5'-Dimethoxytrityl-2'-O-methyluridine-3'-[2-cyanoethyl-N,N-diisopropyl-phosphoramidite] ($U_{me}$-DE), and N$^6$-Benzoyl-5'-Dimethoxytrityl-2'-O-methyladenosine-3'-[2-cyanoethyl-N,N-diisopropyl-phosphoramidite] ($A_{me}$-DE).

Solvent: Anhydrous acetonitrile
Deblock: 2.5% Dichloroacetic acid in dichloromethane
CAP A: 40% acetic anhydride in anhydrous acetonitrile
CAP B: 0.25% Dimethylaminopyridine (DMAP) in anhydrous pyridine
Oxidizer: Genta oxidizer for MAP monomers (25 g Iodine in 0.25% water, 25%, 2-6-lutidine, 73% tetrahydrufuran)
Oxidizer: Commercial (Glen Research) oxidizer for Phosphodiester Activator: 0.45 M tetrazole in Anhydrous acetonitrile
Support bond nucleoside (b) Solid Support Synthesis of 2'-O-Methyl Oligonucleotide with Alternate Methylphosphonate and Phosphodiester Backbone The oligomer was synthesized on an a model 8900 Expedite synthesizer from Biosearch. The methylphosphonamidite monomers $A_{me}$-MAP, $G_{me}$-MAP, $C_{me}$-MAP and $U_{me}$-MAP were placed on ports A, G, C and T respectively with a concentration of 100 mM in acetonitrile. The 2-cyanoethyl phosphoramidite monomers $A_{me}$-DE, $G_{me}$-DE, $C_{me}$-DE, and $U_{me}$-DE for phosphodiester linkage were placed on ports 6, 7, 8 and 9. A low water oxidizer for methylphosphonate coupling was placed on Oxidizer port and a commercial oxidizer (from Glen Research) was placed on Aux port for diester linkage oxidation. The coupling programs for methylphosphonate and diesters at 15 mol scale were as shown in the tables below. The oligomer sequence is from acetyl-transferase gene (CAT) which was as follows;

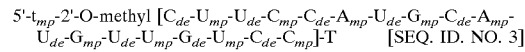
5'-$t_{mp}$-2'-O-methyl [$C_{de}$-$U_{mp}$-$U_{de}$-$C_{mp}$-$C_{de}$-$A_{mp}$-$U_{de}$-$G_{mp}$-$C_{de}$-$A_{mp}$-$U_{de}$-$G_{mp}$-$U_{de}$-$U_{mp}$-$G_{de}$-$U_{mp}$-$C_{de}$-$C_{mp}$]-T    [SEQ. ID. NO. 3]

A thymidine solid-support was used and the n-1 oligomer was synthesized with all the bases in parenthesis being 2'-O-methyl. The 5'-end bases was chosen as deoxy-T due to availability of tritated monomer. To avoid radioactive contamination, the 5'-terminal T was coupled by manual method using syringes instead of synthesizer to push reagents through the solid support. Both non-tritiated and a batch of tritiated oligomer were sized by this procedure.

TABLE IIA

Expedite Coupling Program for 2'-O-Methyl-methylphosphonate (15 umol)

| /* Function | Mode | Amount/Arg1 | Time (sec) Arg2 | Description |
|---|---|---|---|---|
| $Deblocking | | | | |
| 144/* Advance Frac | NA | 1 | 0 | "Event out ON" |
| 0/* Default | WAIT | 0 | 1.5 | "Wait" |
| 141/* Photometer S | NA | 1 | 1 | "START data collection" |
| 16/* Dblk | PULSE | 600 | 20 | "Dblk to column" |
| 38/* Wsh A to Cl | PULSE | 50 | 0 | "Flush system with Wash A" |
| 141/* Photometer S | NA | 0 | 1 | "STOP data collection" |
| 39/* Gas A to Cl | PULSE | 20 | 0 | "Gas A to Cl waste" |
| 144/* Advance Frac" | NA | 2 | 0 | "Event out OFF" |
| 12/* Wsh A | PULSE | 400 | 0 | "Wash A" |
| $Coupling | | | | |
| 1/* Wsh | PULSE | 27 | 0 | "Flush system with Wash" |
| 2/* Act | PULSE | 31 | 0 | "Flush system with Act" |
| 18/* A+Act | PULSE | 35 | 10 | "Monomer + Act to column" |
| 2/* Act | PULSE | 20 | 10 | "Couple monomer" |
| 1/* Wsh | PULSE | 20 | 0 | "Flush system with Wash" |
| $Oxidizing | | | | |
| 15/* OX | PULSE | 135 | 30 | "Oxidizer to column" |
| 12/* Wsh A | PULSE | 100 | 0 | "Flush system with Wash A" |
| $Capping | | | | |
| 13/* Caps | PULSE | 100 | 0 | "Caps to column" |
| 12/* Wsh A | PULSE | 340 | 0 | "End of cycle wash" |

TABLE IIB

Expedite Coupling Program for 2'-O-Methyl-Phosphodiester (15 umol)

| /* Function | Mode | Amount/Arg1 | Time (sec) Arg2 | Description |
|---|---|---|---|---|
| $Deblocking | | | | |
| 144/* Advance Frac | NA | 1 | 0 | "Event out ON" |
| 0/* Default | WAIT | 0 | 1.5 | "Wait" |
| 141/* Photometer S | NA | 1 | 1 | "START data collection" |
| 16/* Dblk | PULSE | 600 | 20 | "Dblk to column" |
| 38/* Wsh A to Cl | PULSE | 50 | 0 | "Flush system with Wash A" |
| 141/* Photometer S | NA | 0 | 1 | "STOP data collection" |
| 39/* Gas A to Cl | PULSE | 20 | 0 | "Gas A to Cl waste" |
| 144/* Advance Frac" | NA | 2 | 0 | "Event out OFF" |
| 12/* Wsh A | PULSE | 400 | 0 | "Wash A" |
| $Coupling | | | | |
| 1/* Wsh | PULSE | 27 | 0 | "Flush system with Wash" |
| 2/* Act | PULSE | 31 | 0 | "Flush system with Act" |
| 18/* A+Act | PULSE | 35 | 28 | "Monomer + Act to column" |
| 18/* A+Act | PULSE | 30 | 180 | "Couple monomer" |

TABLE IIB-continued

Expedite Coupling Program for 2'-O-Methyl-Phosphodiester (15 umol)

| /* Function | Mode | Amount/Arg1 | Time (sec) Arg2 | Description |
|---|---|---|---|---|
| 2/* Act | PULSE | 30 | 100 | "Couple monomer" |
| 1/* Wsh | PULSE | 68 | 0 | "Flush system with Wash" |
| $Oxidizing | | | | |
| 15/* Aux | PULSE | 135 | 30 | "Oxidizer to column" |
| 12/* Wsh A | PULSE | 100 | 0 | "Flush system with Wash A" |
| $Capping | | | | |
| 13/* Caps | PULSE | 100 | 0 | "Caps to column" |
| 12/* Wsh A | PULSE | 340 | 0 | "End of cycle wash" |

(c) Deprotection and Desalting

Dry support was removed from the synthesis column and placed into 10 ml screw top vial and deprotected by the one-pot procedure described below. To the beads was added 4 ml of a solution containing ACN/Ethanol-NH$_4$OH (45:45:10), the mixture was vortexed and allowed to stand at room temperature for 30 minutes. To the mixture was added 4 ml of distilled ethylenediamine and the vial was attached to a rotary mixer and allow to react at room temperature for 6 hours. The solution was removed and diluted with water and neutralized with 6 N HCl. It was further diluted with water to a 5% organics. The sample was then desalted on a C-18 Sep-Pak cartridge (Millipore/Waters, Bedford, Mass.) which had been preswelled and washed with 15 ml each of ACN, 50% ACN in 100 mM triethylammonium bicarbonate (TEAB) and 25 mM TEAB. Following absorption of the oligomer to the column, the column was eluted with 15 ml water then 5 ml of 25% ACN in water, and then 5 ml 50% ACN in water. Each eluant were analyzed for the amount of A260 UV absorbing materials by chromatography on a normal phase Cyclobond HPLC column using a 60% isocratic ACN/50 mM ammonium acetate. Each 15 μmol synthesis normally gives 1,500–2,000 OD units of crude material at 260 nm.

(d) Purification

The oligomer solution was dried down, redissolved in 1,000 uL of 50% ACN/Water and purified on a Semi-Preparative Cyclobond HPLC column. For a baseline separation, about 500 OD's of crude oligomer was chromatographed each time and subsequently concentrated on a Speed-Vac. Two co-evaporations with water was sufficient to remove the ammonium acetate from the oligomer. The non-tritiated oligomer was further analyzed by mass spectroscopy using Electro Spray Ionization. The calculated mass for this oligomer was 6447.5 and the found value was 6448. The tritiated oligomer was further analyzed by HPLC spike of the non-tritiated and side by side PAGE analysis.

Example 26
Preparation of Oligoribonucleosides

Oligoribonucleotides may be synthesized using the following procedures:

The oligoribonucleotides were synthesized using 5'-O-dimethoxytrityl-2'-O-tert-butyldimethylsilyl-3'-O-N,N-diisopropyl-β-cyanoethylphosphoramidite nucleosides (Millipore, Hilford, Mass.). The syntheses were done on a 1 μmole scale with a Milligen 8750 automated DNA synthesizer using standard Milligen phosphoramidite procedures with the exception that the coupling times were extended to 12 minutes to allow adequate time for the more sterically hindered 2'-O-tert-butyldimethylsilyl RNA monomers to react. The syntheses were begun on control-pore glass bound 2'-O-tert-butyldimethylsilyl ribonucleosides purchased from Millipore. All other oligonucleotide synthesis reagents were as described in Millipore's standard protocols.

After synthesis, the oligonucleotides were handled under sterile, RNase-free conditions. Water was sterilized by overnight treatment with 0.5% diethylpyrocarbonate followed by autoclaving. All glassware was baked for at least 4 hours at 300° C.

The oligonucleotides were deprotected and cleaved from the support by first treating the support bound oligomer with 3/1 ammonium hydroxide/ethanol for 15 hours at 55° C. The supernatant, which contained the oligonucleotide, was then decanted and evaporated to dryness. The resultant residue was then treated with 0.6 mL of 1 M tetrabutylammonium fluoride in tetrahydrofuran (which contained 5% or less water) for 24 hours at room temperature. The reaction was quenched by the addition of 0.6 mL of aqueous 2 M triethylammonium acetate, pH 7. Desalting of the reaction mixture was accomplished by passing the solution through a Bio-Rad 10DG column using sterile water. The desalted oligonucleotide was then dried.

Purification of the oligoribonucleotides was carried out by polyacrylamide gel electrophoresis (PAGE) containing 15% 19/1 polyacrylamide/bis-acrylamide and 7 M urea using standard procedures (See Maniatis, T. et al., *Molecular Cloning: A Laboratory Manual*, pages 184–185 (Cold Spring Harbor 1982)). The gels were 20 cm wide by 40 cm long and 6 mm in width. The oligoribonucleotides (60 OD Units) were dissolved in 200 μL of water containing 1.25% bromophenol blue and loaded onto the gel. The gels were run overnight at 300 V. The product bands were visualized by UV backshadowing and excised, and the product eluted with 0.5 M sodium acetate overnight. The product was desalted with a Waters C18 Sep-Pak cartridge using the manufacturer supplied protocol. The product was then $^{32}$P labelled by kinasing and analyzed by PAGE.

Example 27
Preparation of Racemic Methylphosphonate Oligonucleotides

The oligomers were synthesized using 5'-(dimethoxytrityl) deoxynucleoside-3'-[(N,N-diisopropylamino)methyl]-phosphonoamidite monomers. Solid-phase synthesis was performed on methacrylate polymer supports with a Biosearch Model 8750 DNA synthesizer according to the manufacturer's recommendations except for the following modifications: the monomer, were dissolved in acetonitrile at a concentrations of 100 mM, except dG, which was dissolved in 1/1 acetonitrile/dichloromethane at 100 mM. DEBLOCK reagent=2.5% dichloroacetic acid in dichloromethane. OXIDIZER reagent=25 g/L iodine in 0.25% water, 25% 2,6-lutidine, 72.5% tetrahydrofuran. CAP A =10% acetic anhydride in acetonitrile. CAP B=0.625% N,N-dimethylaminopyridine in pyridine.

The dimethoxytriyl group was removed from the oligonucleotide at the end of the synthesis.

The oligonucleotide was then cleaved from the support and deprotected. The support bound oligonucleotide was removed from the synthesis cartridge and placed in a glass 1 dram vial with a screw top. The support was treated for 30 minutes at room temperature with 1 ml of a solution of acetonitrile/ethanol/NH$_4$OH (9/9/1). Then, 1 ml of ethylenediamine was added to the reaction vessel and the reaction allowed 6 hours to go to completion. The supernatant containing the oligonucleotide was then removed from the support and the support rinsed twice with 2 ml of 1/1 acetonitrile/water, when combined with the supernatant. The combined solution was diluted to 30 ml total volume with water and neutralized with approximately 4 ml of 6 N HCL. The neutralized solution was desalted using a Waters C-18 Sep-Pak cartridge which was pre-equilibrated with 10 ml acetonitrile, 10 ml of 50% acetonitrile/100 mM triethylammonium bicarbonate, and 10 ml of 25 mM triethylammonium bicarbonate, sequentially. After the reaction solution was passed through the column it was washed with 30 ml of water. The product was then eluted with 5 ml of 1/1 acetonitrile/water.

The oligonucleotide was purified by HPLC on a reverse phase column (Whatman RAC II) using a gradient of acetonitrile in 50 mM triethylammonium acetate.

Example A
Tm Studies of Oligomers Having an Alternating CT Sequence But Having Different Backbones A series of Oligomers having the same nucleoside sequence (alternating CT with 2'-deoxy sugars and alternating CU with 2'-O-methyl sugars) but having different backbones (different internucleosidyl linkages) were prepared as described in the examples herein. Methylphosphonate dimers (CT) (prepared as described in Example 1A) were used to prepare the 2'-deoxy MP/MP Oligomer. Methylphosphonate (CU) dimers prepared according to Example 2 were used to prepare the 2'-O-Methyl-MP/DE Oligomer. Control oligomers (a) 2'-deoxy all DE, having 2'-deoxy nucleosides and all phosphodiester internucleosidyl intakes and (b) 2'-O-methyl all DE, having 2'-O-methyl nucleosides and all phosphodiester internucleosidyl linkages were purchased from Oligos, Etc.

Hybridization experiments were conducted according to the following procedure:

Annealing reaction mixtures contained equimolar amounts of Oligomer and RNA target Oligomer (2.4 μM total strand concentration), 20 mM potassium phosphate (pH 7.2), 100 mM sodium chloride, 0.1 mM EDTA and 0.03% potassium sarkosylate. The strands were annealed by heating the reaction mixtures to 80° C. and then slowly cooling to 4° C. over about 4 to 6 hours. The annealed samples were then transferred to 1 cm pathlength quartz cuvettes and placed in a Varian Cary 3E UV/Visible Spectrophotometer equipped with a thermostat multicell holder (pre-cooled to 4° C.), temperature controller and temperature probe accessoried. Samples were monitored by measuring absorbance at 260 nm over an increasing temperature gradient (1° C./minute). Data was recorded and processed using a PC computer interface. The temperature was varied from 5° C. to 80° C. at a ramp rate of 1° C./minute. The Tm for each melt profile was determined at the maximum value of the first derivative of the sigmoidal melt transition (the point corresponding to the maximum of the first derivative of the curve corresponding to absorbance versus temperature). Binding affinities (Ka) were determined by applying a non-linear least-squares fit analysis to the sigmoidal melt transition data and assuming a two state model for the termal denaturation process. The following Table II summarizes these results:

TABLE II

Sequence:
5'-CTCTCTCTCTCTCTA-3' (with 2'-deoxy sugars) [SEQ. ID. NO. 1]
5'-CUCUCUCUCUCUCUA-3' (with 2'-o-methyl sugars) [SEQ. ID. NO. 2]

Tm's for Oligomers

| Oligo number | Backbone type | Tm (RNA) | Ka (37° C.) |
|---|---|---|---|
| 2288-1 | Racemic all-methylphosphonate | 34.4° C. | $8.3 \times 10^5$ |
| 2781-1 | 2'-O-methyl racemic all-methylphosphonate | 37.1° C. | $2.1 \times 10^6$ |
| 2782-1 | Alternating racemic MP/DE | 40.6° C. | $6.3 \times 10^6$ |
| 3384-1 | Alternating racemic (2'-deoxy) MP/(2'-O-methyl)DE | 50.1° C. | $3.7 \times 10^8$ |
| 2793-1 | Phosphorothioate | 50.4° C. | $4.6 \times 10^8$ |
| 2784-1 | 2'-O-methyl alternating racemic MP/DE | 59.0° C. | $3.3 \times 10^9$ |
| 2195-1 | Phosphodiester | 60.8° C. | $9.1 \times 10^{11}$ |

Example B
Stability of Oligomers to 5'-Exonuclease Degradation by Snake Venom Phosphodiesterase The following example demonstrates (a) the enhanced nuclease stability of the 2'-deoxy MP(Rp)/DE backbone compared to an all-diester (DE) backbone; and (b) the enhanced nuclease stability of the 2'-O-methyl MP(Rp)/DE backbone compared to the 2'-deoxy MP(Rp)/DE backbone.

Oligomers were evaluated having the following sequence: 5'-CTCTCTCTCTCTCTA-3' [SEQ. ID. NO. 1] (for 2'-deoxy sugars); or 5'-CUCUCUCUCUCUCUA-3' [SEQ. ID. NO. 2] (for 2'-O-methyl sugars).

Snake venom phosphodiesterase I (PDE-I) from crotalus adamanteus was purchased from US Biochemicals, Inc. The all-diester (DE) backbone oligomer was purchased from Oligos Etc. The other oligomers were synthesized as described in the preceding examples.

Aliquots of each oligomer (0.075 A$_{260}$ units) were pipetted into polypropylene microcentrifuge tubes and dried in a Speed-Vac™ vacuum centrifuge (Savant, Inc.). Next, the tubes were placed on ice and aliquots of PDE-I were added to each tube (0.19 unit in 95 μl of 10 mM Tris-HCl, pH 8.8, 2 mM MgCl$_2$, 0.4% glycerol). The zero time point samples were diluted immediately with acetonitrile (35 μl), frozen in a dry ice/isopropanol bath, and stored at –20° C. for analysis at a later time. The remaining samples were then placed in a water bath at 37° C. Samples for each specified time point were then removed form the water bath, diluted with acetonitrile and frozen as described for the zero time point samples.

At the conclusion of the nuclease degradation experiment, the samples were individually thawed and analyzed immediately be reversed phase HPLC using a Beckman System Gold apparatus with a Model 126 binary gradient pump module and a Model 168 Diode Array Detector. The samples were injected onto the column using a manual injector with a 2000 μl sample loop. A Vydac C4 Protein column was used for these experiments (Vydac cat. No. 901019, 4.6 mm i.d. ×250 mm long). Elution was done with a dual solvent system: Buffer A=1% acetonitrile in 50 mM triethyl ammonium acetate (TEAA, pH 7.0); Buffer B=50% acetonitrile in 50 mM TEAA (pH 7.0). Solvent flow rates were increased from 0.05 to 1.0 ml/minutes over the first minute of the run and then held at 1.0 ml/minute for the remainder of the run. Gradient conditions for each backbone were as follows: All-DE backbone-5–25% Buffer B (2.5–9 minute), 25–45% Buffer B (9.0–22.5 minute) 45–100% Buffer B (22.5–28.0 minute); 2'-deoxy MP(Rp)/DE backbone-5–35% Buffer B (2.5–12.5 minute), 35–50% Buffer B (12.5–22.5 minute), 50–100% Buffer B (22.5–27.5 minute); 2'-O-methyl MP(Rp)/DE backbone-5–50% Buffer B (2.5–17.5 minute), 50–65% Buffer B (17.5–27.5 minute), 65–100% Buffer B (27.5–31.0 minute). Average retention times for each backbone oligomer (undegraded) were as follows:

| | |
|---|---|
| All-DE | 15.7 minutes |
| 2'-deoxy MP(Rp)/DE | 18.5 minutes |
| 2'-O-methyl MP(Rp)/DE | 18.6 minutes |

Degradation was determined by the appearance of earlier eluting peaks and a decrease in area (or complete loss) of the peak corresponding to the full-length oligomer. Percent degradation was determined by comparing the peak heights and peak areas for each time point at 37° C. to the zero time point. The half-lives for each oligomer in the presence of PDE-I were then determined by plotting log (% full-length) versus time and finding the value corresponding to log (50%)=1.699. The following results were obtained from two separate experiments.

TABLE III

Sequence:
5'-CTCTCTCTCTCTCTA-3' (with 2'-deoxy sugars)  [SEQ. ID. NO. 1]
5'-CUCUCUCUCUCUCUA-3' (with   [SEQ. ID. NO. 2]
2'-0-methyl sugars)

| Oligomer | T½ |
|---|---|
| (a) Comparison of All-DE backbone oligomer to 2'-deoxy-MP(Rp)/DE backbone oligomer. | |
| All-DE | <1 minute |
| 2'-deoxy MP(Rp)/DE | 12.5 minutes |
| (b) Comparison of 2'-deoxy MP(Rp)/DE backbone oligomer to 2'-O-methyl MP(Rp)/DE backbone oligomer. | |
| 2'-deoxy MP(Rp)/DE | 10 minutes |
| 2'-O-methyl MP(Rp)/DE | 350 minutes |

Example C
Stability of 2'-deoxy MP(Rp)/DE Oligomer in Cytoplasmic Lysate From HeLa Cells This example demonstrates that the 2'-deoxy mixed backbone oligomer is completely stable in HeLa cell lysate within the limits of detection over the time course of the experiment.

HeLa cell cytoplasmic lysate was purchased from Endotronics, Inc. (Minneapolis, Minn.). This preparation is a hypotonic bounce lysis in 5× the packed cell volume. It was buffered to pH 6.0 by adding 0.4 ml of 2-(N-morpholino) ethanesulfonate (MES, 0.5 M solution, pH 6.0) to 3.6 ml of cell lysate on ice and mixing with mild agitation.

Aliquots of oligomer were dried and then diluted with HeLa cell lysate (95 µl) as described in the preceding example. Samples were then incubated at 37° C. and analyzed as described in Example B.

TABLE IV

Sequence:
5'-CTCTCTCTCTCTCTA-3' (with 2'-deoxy sugars)  [SEQ. ID. NO. 1]
5'-CUCUCUCUCUCUCUA-3' (with   [SEQ. ID. NO. 2]
2'-0-methyl sugars)

| Oligomer | T½ |
|---|---|
| All-DE | 1.4 hours |
| 2'-deoxy MP(Rp)/DE | No degradation observed over 72 hours incubation at 37° C. |

Example D
Stability of 2'-deoxy MP(Rp)/DE and 2'-O-methyl MP(Rp)/DE Backbone Oligomers in Cytoplasmic Lysate From African Green Kidney COS-7 Cells The following example demonstrates that a 2'-deoxy MP(Rp)/DE and 2'-O-methyl MP(Rp)/DE backbone oligomers are at least 500 times more stable to degradation in COS-7 cell lysate then the corresponding All-DE backbone oligomers having the same sequence.

COS-7 cell lysate for these experiments was prepared as follows. COS-7 cells were grown to 90% confluency and then harvested in the presence of 0.25% trypsin. The cell pellets were swashed twice with phosphate buffered saline and then frozen overnight at −20° C. Next, the pellets were resuspended in approximately an equal volume of lysis buffer (2.5 mM HEPES, pH 7.2, 2.0 mM $MgCl_2$, 0.1% NP-40), drawn up and down ten times through a sterile 1 ml polypropylene pipette, and then centrifuged at 10,000 XG for 5 minutes. Approximately 40% of the resulting supernatant was then used to lyse the cell pellet in a dounce homogenizer (Type A pestle) with twenty strokes. This suspension was then centrifuged as above and the supernatant was combined with the rest of the supernatant from the first resuspension. The resulting solution represents predominantly cytosolic lysate without any nuclear debris and is approximately 1–1.5 times the volume of the original packed cell pellet. Aliquots from the resulting cell lysate were buffered with either 25 mM Tris-acetate (final pH 7.4) or 25 mM MES (final pH 6.0) prior to incubation with oligomer.

Aliquots of each oligomer (0.075) $A_{260}$ unit) were dried in sterile polypropylene microcentrifuge tubes and then resuspended in 10 µl of COS-7 cell lysate on ice. Water (90 µl) and acetonitrile (35 µl) were added immediately to the zero time samples and they were frozen in a dry ice/ethanol bath and stored at −20° C. for later analysis. The remaining samples were then incubated in a water bath at 37° C. At specified time points, samples were removed from the water bath, diluted with water and acetonitrile and frozen exactly as described for the zero time point controls.

Following the incubations with cell lysate, the samples were individually thawed, diluted with water (535 µl) and analyzed immediately by reversed phase HPLC as described in Example B. Degradation was determined from the resulting chromatograms as described in Example 26. The results are summarized in Table V below:

TABLE V

Sequence:
5'-CTCTCTCTCTCTCTA-3' (with 2'-deoxy sugars) [SEQ. ID. NO. 1]
5'-CUCUCUCUCUCUCUA-3' (with 2'-0-methyl sugars) [SEQ. ID. NO. 2]

| Oligomer | T½ |
| --- | --- |
| All-DE backbone oligomer | <5 minutes No full length oligomer remained after 5 minutes of incubation at 37° C. |
| 2'-O-methyl all-DE backbone | ~5 hours. |
| 2'-deoxy MP(Rp)/DE backbone | ~35 hours. (Approximately 35% loss of peak corresponding to full-length oligomer after 24 hours incubation at 37° C.) |
| 2'-O-methyl MP(Rp)/DE | 100% stable over a 24 hour incubation at 37° C. |

Example E

Stability of 2'-deoxy MP(Rp)/DE Backbone Oligomer in Bacterial Cell Lysate From *Escheria coli*

The following example demonstrates that a 2'-deoxy MP(Rp)/DE oligomer is at least 2,000 fold more stable than an all-DE oligomer having the same sequence in cell lysate from *E. coli*.

*E. coli* cell lysate was prepared as follows. Approximately $2 \times 10^{11}$ cells were pelleted by centrifugation, resuspended in 10 ml of Tris-HCl (50 mM, pH 7.5) and incubated at room temperature for five minutes. Next, dithiothreitol and lysozyme were added to final concentrations of 2 mM and 1 mg/ml, respectively, and the resulting suspension was incubated at 37° C. for 30 minutes. The mixture was then sonicated briefly ten times on ice and centrifuged at 7,000 rpm for 20 minute. Based on visual inspection, it was estimated that this procedure had not sufficiently lysed the cells, so the supernatant (vol.=5 ml) was collected and stored at 4° C. and the cell pellet was resuspended in 1 ml of Tris-HCl (50 mM, pH 7.5). The resuspended cell pellet was exposed to five rounds of freeze/thaw, sonicated briefly to break up the chromosomal DNA, and then centrifuged at 8.000 rmp for 5 minutes. The resulting supernatant (approx. 70 μl) was then combined with the supernatant from the previous step (approx. 5 ml) and centrifuged at 6,000 XG for 5 minutes to pellet any residual debris. The final supernatant was estimated to contain approximately 50% lysed cells in approximately 57 times the original cell pellet volume (100 μl).

Aliquots of the oligomers (0.050 $A_{260}$ units) were dried in sterile polypropylene microcentrifuge tubes and resuspended in 95 μl of cell lysate on ice. Incubations at 37° C., HPLC analysis, and quantitation of oligomer degradation were done exactly as described in Example B. The results are summarized below:

TABLE VI

Sequence:
5'-CTCTCTCTCTCTCTA-3' (with 2'-deoxy sugars) [SEQ. ID. NO. 1]
5'-CUCUCUCUCUCUCUA-3' (with 2'-0-methyl sugars) [SEQ. ID. NO. 2]

| Oligomer | T½ |
| --- | --- |
| All-DE | 1–3 minutes. |
| 2'-deoxy MP(Rp)/DE | ~65 hours. (84.5% full-length oligomer remained after 20.5 hours incubation at 37° C.) |

Example F

Stability of 2'-deoxy MP(Rp)/DE Backbone Oligomer in Bacterial Cell Lysate from *Staphylococcal aureus*

The following example demonstrates that a 2'-deoxy MP(Rp)/DE oligomer is at least 400 fold more stable than an all-DE oligomer having the same sequence in cell lysate from *S. aureus*.

*S. aureus* cell lysate was prepared at described for *E. coli* in Example #4 except with the following modifications: (i) the lysis was conducted with a cell pellet containing approximately $4 \times 10^{10}$ cells; (ii) lysostaphin was used instead of lysozyme (500 units, Sigma, Inc.); and (iii) a total of 10 freeze/thaw cycles were used instead of 5.

Incubation with oligomers at 37° C., HPLC analysis and determination of oligomer degradation from the chromatograms were conducted exactly as described for the experiment with *E. coli* in Example E. The results are summarized below:

TABLE VII

Sequence:
5'-CTCTCTCTCTCTCTA-3' (with 2'-deoxy sugars) [SEQ. ID. NO. 1]
5'-CUCUCUCUCUCUCUA-3' (with 2'-0-methyl sugars) [SEQ. ID. NO. 2]

| Oligomer | T½ |
| --- | --- |
| All-DE | 13 minutes |
| 2'-deoxy MP(Rp)/DE | ~75 hours. (86.4% full-length oligomer remained after 20.5 hours |

Example G

Stability of a [$^3$H]Labeled All-2'-O-Methyl MP/DE Oligomer Following Single Dose Intravenous Administration Oligomers used in this study had the following sequence:

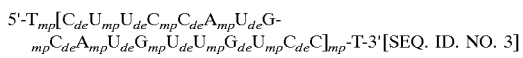

5'-T$_{mp}$[C$_{de}$U$_{mp}$U$_{de}$C$_{mp}$C$_{de}$A$_{mp}$U$_{de}$G-$_{mp}$C$_{de}$A$_{mp}$U$_{de}$G$_{mp}$U$_{de}$U$_{mp}$G$_{de}$U$_{mp}$C$_{de}$C]$_{mp}$-T-3' [SEQ. ID. NO. 3]

wherein all nucleosides within the brackets were 2'-O-methylribosides. The oligomer 3311-1 termed "[$^3$H] oligomer" had a tritiated methyl group in the methylphosphonate linkage linking the 5'-C nucleoside and the adjacent 2'-O-methyl C nucleoside. The oligomer 3311-2 termed "cold oligomer" has no tritium label.

As set forth below, two different formulations of the above oligomer were used for animal dosing and sampling.

(a) Blood levels. 2.5 mg of 3311-2 ("cold oligomer") was dissolved in 500 μL of a sterile solution of 5% dextrose in distilled water. 1.0 mg of 3311-1 ("[³H]oligomer", specific activity +400 Ci/mole) was dissolved in 200 μL of a sterile solution of 5% dextrose in distilled water. Both solutions were mixed together to give a final oligomer concentration of 5 mg/m: and a radioactivity concentration of 111 μCi/mL. The resulting sample was shipped on ice to an investigator for animal dosing and sampling.

Two male Sprague-Dawley rats (approximately 0.24 kg each) were dosed with this oligomer mixture (270 μL per animal, 5 mg/kg, 30 μCi) via an indwelling tail vein cannula. Blood samples (ca. 250 μL) were taken via the cannula at 2, 5, 10, 20, 30, 45 minutes, and 1, 1.5, 3 and 5 hours post-dosing. Blood samples were transferred immediately to Microtainers and centrifuged to yield serum. Serum samples were frozen on dry ice and then shipped on dry ice to a laboratory for analysis.

(b) Urine/feces. 0.6 mg of 3311-2 ("cold oligomer") and 0.6 mg of 3311-3 1 ("[³H] oligomer", specific activity—400 Ci/mole) were dissolved in 600 μL of 1× phosphate buffered saline (prepared from 10× stock, GIBCO) and sent on ice an investigator for dosing and sampling. Upon arrival, this sample was stored at 4° C.

Male Sprague-Dawley rats, approximately 8–10 weeks old at the time of dosing, were purchased from Taconic, Inc. (Germantown, N.Y.). At least 24 hours prior to dosing, two animals were surgically implanted with chronic, indwelling, S-27 Jugular Vein Catheters (IITC, Inc., Woodland Hills, Calif.). On the day of dosing, the animals were weighed to the nearest gram. The oligomer sample was drawn into an appropriately sized plastic syringe to allow measurement to 0.1 mL of the required dose. Dosing syringes were weighed immediately prior to and immediately after dosing, and the exact quantity of oligomer administered was determined gravimetrically. The actual dose administered to each rat was between 0.44 and 0.54 mg (1.27 to 1.53 mg/kg body weight). Urine and feces were taken at 4, 8, 24 and 48 hours post-dosing. These samples were frozen immediately upon excretion and kept frozen for the entire collection period the urine samples were then thawed briefly ad aliquots were removed to determine total radioactivity. The urine samples were then sent frozen on dry ice to a laboratory for analysis.

(c) Sample treatment and analysis. Serum samples were thawed on ice and two aliquots (5 μL) were withdrawn and added to scintillation fluid for determination of total radioactivity by liquid scintillation counting. Aliquots (100 μL) of serum were processed for HPLC analysis as follows. First, 1.4 μL of 100 mM EDTA (disodium salt) was added along with 0.1 OD$_{260}$ unit of 3311-2 ("cold oligomer") for use as an internal standard. Next, 100 μL of a 1% solution of NP40 detergent in acetonitrile was added and the samples were spun in a microcentrifuge to remove precipitated proteins. The supernatants were withdrawn and transferred to separate containers and dried under vacuum. The resulting residues were then resuspended in 100 μL of 50 mM triethyl ammonium acetate buffer (TEAA, pH 7).

Urine samples were processed by adding 10 μL of 50 mM TEAA buffer (pH 7.0) and 10 μL of 1.0 OD$_{260}$ unit/mL of 3311-2 ("cold oligomer") as an internal standard to 100 μL of urine.

HPLC analysis was conducted on a Beckman System Gold™ apparatus equipped with a Model 126 Dual Gradient solvent module and a Model 168 Diode Array detector. A Packard Flo/One beta detector was used for determination of tritium counts. Chromatography was conducted with a Vydac C4 column using a linear gradient of 2.5% to 45% acetonitrile in TEAA buffer (pH 7.0), flow rate =1.0 mL/min. The full length oligomer was identified by monitoring at 260 nm and noting the elution time of the internal standard (3311-2). The radioactivity in the peak corresponding to the same retention time was integrated and compared to total integrated radioactivity to determine the percent full length oligomer in each sample the following table summarizes the results:

TABLE IX

A. Blood Samples:

| Time (min) | Avg. Concentration (μg/mL) | % Intact Oligomer in Serum* |
|---|---|---|
| 2 | 26.09 | >95% |
| 5 | 12.04 | >95% |
| 10 | 6.57 | >95% |
| 20 | 3.11 | >95% |
| 30 | 2.09 | >95% |
| 60 | 0.82 | >95% |

B. Urine samples:

| Time (hrs) | Cumulative % Injected Dose | % Intact Oligomer* |
|---|---|---|
| 0–4 | 50.4 | 76.72 |
| 4–8 | 58-1 | 42.79 |
| 8–24 | 61.1 | 28.51 |
| 24–48 | 63.7 | 28.71 |

*The peak corresponding to the full-length oligomer contained greater than about 95% of the total integrated radioactivity for each sample tested.

This example demonstrated that an all-2'-O-methyl, alternating MP/DE oligomer was essentially undegraded in the blood up to about 1 hour. Also, a significant portion of the oligomer was excreted into the urine in undegraded form. We conclude from this example that oligomers having this particular backbone type are sufficiently stable in vivo for pharmaceutical applications.

Example H
Nuclease Stability Studies of Various Backbone Modified (Non-Chimeric) Oligomers In each of the experiments described in this example, various backbone modified oligomers were evaluated having the following sequence: 5'-CTCTCTCTCTCTCTA-3' [SEQ. ID. NO. 1] (for 2'-deoxy sugars); or 5'-CUCUCUCUCUCUCUA-3' [SEQ. ID. NO. 2] (for 2'-O-methyl sugars). The all-diester (DE) backbone oligomer was purchased from Oligos Etc. The other backbone oligomers were synthesized as described in the preceding examples.

(a) Stability studies in the presence of purified snake venom phosphodiesterase. Snake venom phosphodiesterase I (PDE-I) from crotalus adamanteus was purchased from US Biochemicals, Inc. Aliquots of each oligomer (0.075 A$_{260}$ units) were pipetted into polypropylene microcentrifuge tubes and dried in a Speed-Vac™ vacuum centrifuge (Savant, Inc.). Next, the tubes were placed on ice and aliquots of PDE-I were added to each tube (0.1 unit/mL in 95 μL of 10 mM Tris-HCl, pH 8.8, 2 mM MgCl$_2$, 0.4% glycerol). The zero time point samples were diluted immediately with acetonitrile (35μL), frozen in a dry ice/isopropanol bath, and stored at −20° C. for analysis at a later time. The remaining samples were then placed in a water bath at 37° C. Samples for each specified time point were then removed from the water bath, diluted with acetonitrile and frozen as described for the zero time point samples.

At the conclusion of the nuclease degradation experiment, the samples were individually thawed and analyzed immediately by reversed phase HPLC using a Beckman System Gold apparatus with a Model 126 binary gradient pump module and a Model 168 Diode Array Detector. The samples were injected onto the column using a manual injector with a 2000 μL sample loop. A Vydac C4 Protein column was used for these experiments (Vydac cat. no. 901019, 4.6 mm i.d. ×250 mm long). Elution was done with a dual solvent system: Buffer A=1% acetonitrile in 50 mM triethyl ammonium acetate (TEAA, pH 7.0); Buffer B=50% acetonitrile in 50 mM TEAA (pH 7.0). Solvent flow rates were increased from 0.05 to 1.0 mL/min. over the first minute of the run and then held at 1.0 mL/min. for the remainder of the run. Gradient conditions for each backbone were as follows: All-DE backbone-5–25% Buffer B (2.5–9 min.), 25–45% Buffer B (9.0–22.5 min.) 45–100% Buffer B (22.5–28.0 min.); 2'-deoxy MP($R_p$)/DE backbone-5–35% Buffer B (2.5–12.5 min.), 35–50% Buffer B (12.5–22.5 min.), 50–100% Buffer B (22.5–27.5 min.); 2'-O-methyl MP($R_p$)/DE backbone-5–50% Buffer B (2.5–17.5 min.), 50–65% Buffer B (17.5–27.5 min), 65–100% Buffer B (27.5–31.0 min.). Average retention times for each backbone oligomer (undegraded) were as follows:

All-DE: 15.7 min.

2'-deoxy MP($R_p$)/DE: 18.5 min.

2'-O-methyl MP($R_p$)/2'-O-methyl DE: 18.6 min.

Degradation was determined by the appearance of earlier eluting peaks and a decrease in area (or complete loss) of the peak corresponding to the full-length oligomer.

(b) Stability studies in HeLa cell lysates. HeLa cell cytoplasmic lysate was purchased from Endotronics, Inc. (Minneapolis, Minn.). This preparation is a hypotonic dounce lysis in 5× the packed cell volume. It was buffered to pH 6.0 by adding 0.4 mL of 2-(N-morpholino) ethanesulfonate (MES, 0.5 M solution, pH 6.0) to 3.6 mL of cell lysate on ice and mixing with mild agitation. Aliquots of oligomer were dried and then diluted with HeLa cell lysate (95 μL) as described in the preceding example. Samples were then incubated at 37° C. and analyzed by reversed-phase HPLC exactly as described in the preceding example.

(c) Stability studies in cell lysate from African Green Monkey Kidney COS-7 cells. COS-7 cell lysate for these experiments was prepared as follows. COS-7 cells were grown to 90% confluency and then harvested in the presence of 0.25% trypsin. The cell pellets were washed twice with phosphate buffered saline and then frozen overnight at −20° C. Next, the pellets were resuspended in approximately an equal volume of lysis buffer (2.5 mM HEPES, pH 7.2, 2.0 mM $MgCl_2$, 0.1% NP-40), drawn up and down ten times through a sterile 1 mL polypropylene pipette, and then centrifuged at 10,000×G for 5 minutes. Approximately 40% of the resulting supernatant was then used to lyse the cell pellet in a dounce homogenizer (Type A pestle) with twenty strokes. This suspension was then centrifuged as above and the supernatant was combined with the rest of the supernatant from the first resuspension. The resulting solution represents predominantly cytosolic lysate without any nuclear debris and is approximately 1–1.5 times the volume of the original packed cell pellet. Aliquots from the resulting cell lysate were buffered with either 25 mM Tris-acetate (final pH 7.4) or 25 mM MES (final pH 6.0) prior to incubation with oligomer. Aliquots of each oligomer (0.075 $A_{260}$ unit) were dried in sterile polypropylene microcentrifuge tubes and then resuspended in 10 μL of COS-7 cell lysate on ice. Water (90 μL) and acetonitrile (35 μL) were added immediately to the zero time samples and they were frozen in a dry ice/ethanol bath and stored at −20° C. for later analysis. The remaining samples were then incubated in a water bath at 37° C. At specified time points, samples were removed from the water bath, diluted with water and acetonitrile, and frozen exactly as described for the zero time point controls. Following the incubations with cell lysate, the samples were individually thawed, diluted with water (535 μL) and analyzed immediately by reversed phase HPLC as described above.

(d) Stability studies in cell lysate from *Escherichia coli*. *E. coli* cell lysate was prepared as follows. Approximately $2 \times 10^{11}$ cells were pelleted by centrifugation, resuspended in 10 mL of Tris-HCl (50 mM, pH 7.5) and incubated at room temperature for five minutes. Next, dithiothreitol and lysozyme were added to final concentrations of 2 mM and 1 mg/mL, respectively, and the resulting suspension was incubated at 37° C. for 30 min. The mixture was then sonicated briefly ten times on ice and centrifuged at 7,000 rpm for 20 min. Based on visual inspection, it was estimated that this procedure had not sufficiently lysed the cells, so the supernatant (vol.=5 mL) was collected and stored at 4° C. and the cell pellet was resuspended in in 1 mL of Tris-HCl (50 mM, pH 7.5). The resuspended cell pellet was exposed to five rounds of freeze/thaw, sonicated briefly to break up the chromosomal DNA, and then centrifuged at 8,000 rpm for 5 min. The resulting supernatant (approx. 700 μL) was then combined with the supernatant from the previous step (approx. 5 mL) and centrifuged at 6,000×G for 5 min. to pellet any residual debris. The final supernatant was estimated to contain approximately 50% lysed cells in approximately 57 times the original cell pellet volume (100 μL). Aliquots of the oligomers (0.050 $A_{260}$ units) were dried in sterile polypropylene microcentrifuge tubes and resuspended in 95 μL of cell lysate on ice. Incubations at 37° C., HPLC analysis, and quantitation of oligomer degradation were done exactly as described above.

(e) Stability studies in cell lysate from *Staphylococcal aureus*. *S. aureus* cell lysate was prepared as described above for *E. coli* except with the following modifications: (i) the lysis was conducted with a cell pellet containing approximately $4 \times 10^{10}$ cells; (ii) lysostaphin was used instead of lysozyme (500 units, Sigma, Inc.); and (iii) a total of 10 freeze/thaw cycles were used instead of five. Incubation with oligomers at 37° C., HPLC analysis and determination of oligomer degradation from the chromatograms were conducted exactly as described for the experiment with *E. coli* in the example above.

Results. Percent degradation was determined by comparing the peak heights and peak areas for each time point in each experiment to the zero time point controls. The half-lives for each oligomer in the presence of PDE-I were then determined by plotting log(% full-length) versus time and finding the value corresponding to log(50%)=1.699. The following table summarizes the results from these experiments:

| Half-life of Analog | Normal Phospho-diester | 2'-O-Methyl RNA | MP(R$_p$)/DE Alternating | Alternating 2'-O-Methyl MP(R$_p$)/ 2'-O-methyl DE |
|---|---|---|---|---|
| 10% Fetal Calf Serum, pH 8 | 12 min. | 40 min. | 5 Hrs. | >300 Hrs. |
| Green Monkey Kidney Cell Lysate, pH 6.0 | <10 min. | ~5 Hrs. | ~25 Hrs. | Stable* |
| Green Monkey Kidney Cell Lysate, pH 7.4 | <5 min. | ~5 Hrs. | ~20 Hrs. | Stable* |
| E. coli Cell Lysate | 1–3 min. | 1.2 Hrs. | ~65 Hrs. | Stable* |
| S. Aureus Cell Lysate | 13 min. | ~20 Hrs. | ~75 Hrs. | Stable* |
| Snake Venom Phosphodi-esterase | 15 min. | 2.5 min. | 167 min. | Stable* |

*No detectable degradation after 24 hour incubation.

Example H

Replacement of Phosphodiester Bonds in a Racemic Methylphosphonate Oligomer Enhances Binding Stability The following oligomers [SEQ. ID. NO. ] were tested for their ability to bind a complementary RNA target. Each has the same nucleotide sequence but with a different number of phosphodiester and/or methylphosphonate linkages.

| Oligomer No. | Sequence and Backbone | # DE bonds |
|---|---|---|
| 1036 | 5'-GpAmTmAmTmCmTmGmCmGmGmTmGmTmCmCmAmT-3' | 1 |
| 1362 | 5'-GpAmTmAmTdCmTmGpCmGmGmTmGmTpCmCmAmT-3' | 4 |
| 1361 | 5'-GpAmTmAmTmCpTmGmCpGmGmTmGmTmCpCpAmT-3' | 5 |
| 1359 | 5'-GpAmTpAmTpCmTpGmCmGmGmTpGmTpCmCmAmT-3' | 6 |
| 1363 | 5'-GpAmTpAmTpCpTpGmCpGmGmTpGmTpCpCpAmT-3' | 10 |

An RNA target containing a tandem array of complementary target sequences connected by noncomplementary sequences (170 nt long) was prepared from synthetic DNA oligonucleotides by standard closing techniques.

Each of the test oligomers (above) was end-labeled with $^{32}$p using [λ-32P] ATP and T4 polynucleotide kinase. The resulting labeled oligomers were purified on a Nensorb-20 column (New England Nuclear/DuPont) according to the manufacturer's specifications. The final specific activity of each oligomer ranged between 2×10$^6$ and 4×10$^6$ cpm/pmol (Cerenkov radiation). Annealing reactions were prepared with one of the test oligomers (100,000 cpms) and 250 pmols of RNA target in 20 mM potassium phosphate, 0.03% potassium sarkosylate, 0.1 mM EDTA, pH 7.2, total volume—200 μL. These annealing reactions were heated to 80° C. and then cooled slowly to 4° C. over a period of about 4 to 6 hours. Next, 20 μL aliquots from each tube were transferred to separate tubes containing 0.5 mL of 0.1 M sodium phosphate, 0.1% Triton X-100, pH 6.8. This transfer step was done on ice. The resulting tubes were individually heated at various temperatures "denaturation temperatures", ranging from 10 to 70° C.) in a circulating water bath for five minutes and then quickly cooled by immersion in crushed ice. Next, 10 μL of Amine BioMag (Advanced Magnetics, Inc., Cat. No. M-4100, 50 mg/mL stock in water) was added to the tube and it was vortexed briefly and placed back on ice for 5 minutes. During this time period, the RAN target strands (both free and bound) separated onto the magnetic support. Control experiments showed that negligible amounts of unhybridized oligomers bound to the magnetic support under these conditions. Thus, the amount of radioactivity bound to the support was proportional to the amount of hybridized oligomer remaining at each denaturation temperature after five minutes. A curve was then plotted for the percentage of hybridized oligomer remaining at each denaturation temperature. The thermal dissociation temperature (Td) was defined as the temperature at which 50% of the bound oligomer had denatured away from the RNA target. The following table summarizes the results from this experiment.

| Seq. No. | # DE Bonds | Td (°C.) | ΔTd/DE Bond |
|---|---|---|---|
| 1036 | 1 | 29.3 | — |
| 1362 | 4 | 30.7 | 0.5 |
| 1361 | 5 | 32.2 | 0.7 |
| 1359 | 6 | 34.0 | 0.9 |
| 1363 | 10 | 45.2 | 1.8 |

We claim:

1. A method for making a synthetic Oligomer which hybridizes to an RNA target sequence, said method comprising the steps of:

(a) identifying a single stranded RNA target sequence; and (b) synthesizing a synthetic Oligomer having a mixed nucleoside base sequence and having alternating racemic phosphonate internucleosidyl linkages selected from the group consisting of lower alkyl- and aryl-phosphonate internucleosidyl linkages and lower alkyl- and arylphosphonothioate internucleosidyl linkages and non-phosphonate internucleosidyl linkages and wherein the Oligomer is substantially complementary to said identified RNA target sequence.

2. A method according to claim 1 wherein said phosphonate linkages are lower alkylphosphonate linkages having lower alkyl groups having of 1 to 3 carbon atoms.

3. A method according to claim 2 wherein said lower alkylphosphonate linkages are methylphosphonate linkages.

4. A method according to claim 3 wherein the nucleosides of said oligomer have 2'-substituted ribosyl groups as sugar moieties selected from the group consisting of 2'-O-alkylribosyl of 1 to 10 carbon atoms, 2'-halo-ribosyl, 2'-O-alkenyl ribosyl of 3 to 6 carbon atoms and 2'-deoxyribosyl.

5. A method according to claim 1 wherein said non-phosphonate linkages are selected from the group consisting of phosphodiester, phosphotriester, phosphorothioate, phosphorodithioate, phosphoramidate, phosphorofluoridate, boranophosphate, formacetal and silyl.

6. A method according to claim 1 wherein said Oligomer is synthesized by linking together nucleoside dimers of the formula:

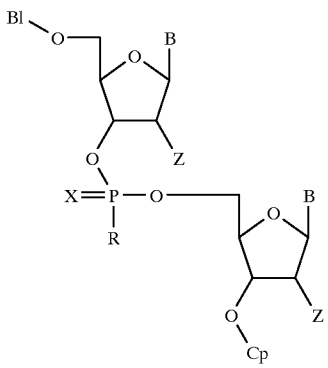

wherein X is oxygen or sulfur, R is alkyl of from 1 to 3 carbon atoms or aryl; Z is hydrogen, alkoxy of from 1 to 10 carbon atoms, halogen or alkenyloxy of 3 to 6 carbon atoms; B is an independently selected optionally protected purine or pyrimidine base; Bl is a blocking group and Cp is a coupling group.

7. A method according to claim 6 wherein X is oxygen and R is methyl.

8. A method according to claim 7 wherein Z is hydrogen or methoxy.

9. A method according to claim 8 wherein the non-phosphonate linkages are phosphodiester linkages.

10. A method according to claim 9 wherein Z is methoxy.

11. A synthetic Oligomer having activity in preventing or interfering with expression or translation of a single stranded RNA target sequence which is a synthetic Oligomer having a mixed nucleoside base sequence and having alternating racemic phosphonate racemic phosphonate internucleosidyl linkages selected from the group consisting of lower alkyl- and aryl-phosphonate internucleosidyl linkages and lower alkyl-and arylphosphonothioate internucleosidyl linkages and non-phosphonate internucleosidyl linkages and wherein the Oligomer is substantially complementary to said identified RNA target sequence.

12. An oligomer according to claim 11 wherein said phosphonate linkages are methylphosphonate linkages.

13. An oligomer according to claim 12 wherein said non-phosphonate linkages are selected from the group consisting of phosphodiester, phosphotriester, phosphorothioate, phosphorodithioate, phosphoramidate, phosphorofluoridate, boranophosphate, formacetal and silyl.

14. An oligomer according to claim 13 wherein the nucleosides of said oligomer have 2'-O-methyl ribosyl groups as sugar moieties.

15. An oligomer according to claim 11 wherein the nucleosides of said oligomer have 2'-O-alkylribosyl groups as sugar moieties.

16. A synthetic Oligomer preparation consisting of oligomers having a mixed nucleoside base sequence and having alternating racemic phosphonate internucleosidyl linkages selected from the group consisting of lower alkyl- or arylphosphorothioate linkages and non-phosphonate linkages, wherein the oligomers are complementary to a RNA target sequence, and wherein the oligomer preparation demonstrates enhanced "net" binding affinity for the complementary RNA target sequence in comparison to a racemic all-phosphonate oligomer of the same sequence.

17. A method for preparing an Oligomer having a predetermined mixed base sequence of nucleoside units and having racemic phosphonate internucleosidyl linkages mixed with non-phosphonate internucleosidyl linkages wherein the phosphonate internucleosidyl linkages are interspersed between single non-phosphonate internucleosidyl linkages, which method comprises linking together individual nucleoside dimers, trimers or tetramers having phosphonate internucleosidyl linkages.

18. A method for preparing an Oligomer having a predetermined mixed base sequence of nucleotide units and having alternating racemic phosphonate internucleosidyl linkages and non-phosphonate internucleosidyl linkages, which method comprises linking together individual nucleoside dimers, trimers or tetramers having phosphonate internucleosidyl linkages.

19. A synthon of the formula:

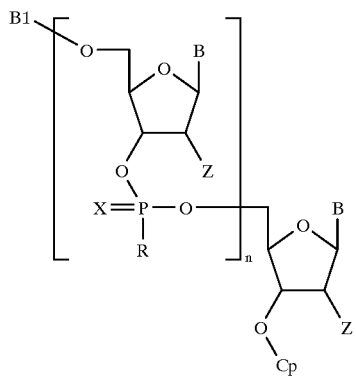

wherein X is oxygen or sulfur, R is alkyl of 1 to 3 carbon atoms or aryl; Z is hydrogen, alkoxy of 1 to 10 carbon atoms, halogen or alkenyloxy of 3 to 6 carbon atoms; B is an independently selected and optionally protected purine or pyrimidine base; Bl is a blocking group; n is 1, 2 or 3 and Cp is a coupling group.

20. A synthon according to claim 19 wherein Z is alkoxy.

21. A synthon according to claim 20 wherein Z is methoxy.

* * * * *

UNITED STATES PATENT AND TRADEMARK OFFICE
CERTIFICATE OF CORRECTION

PATENT NO. : 5,986,083
DATED : November 16, 1999
INVENTOR(S) : Brian P. Dwyer, Lyle John Arnold, Jr. and Mark Alan Reynolds It is certified that error appears in the above-identified patent and that said Letters Patent is hereby corrected as shown below:

Column 54,
Line 14, "...phosphorothioate..." should be corrected to be spelled as
-- phosphonothioate --

Lines 20-28, Claim 17, should be deleted.
Lines 29-35, Claim 18, should be renumbered to Claim 17.
Lines 36-59, Claim 19, should be included in the issued patent and renumbered as Claim 18.

Signed and Sealed this

Third Day of August, 2004

JON W. DUDAS
*Acting Director of the United States Patent and Trademark Office*